(12) United States Patent
Plumptre et al.

(10) Patent No.: US 9,533,107 B2
(45) Date of Patent: Jan. 3, 2017

(54) DRUG DELIVERY DEVICE WITH BIASING TRACK FOR TRANSMITTING LOAD TO ROTATABLE DRIVE MEMBER ENABLING SUBSEQUENT DOSE DISPENSE

(75) Inventors: David Plumptre, Droitwich Spa (GB); Andrew Mark Lindsay, Hinckley (GB); Catherine Anne Macdonald, Ashby-de-la-Zouch (GB); Robert Veasey, Leamington Spa (GB); Christopher Jones, Tewkesbury (GB); Garen Kouyoumjian, Leamington Spa (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1286 days.

(21) Appl. No.: 13/395,897

(22) PCT Filed: Sep. 29, 2010

(86) PCT No.: PCT/EP2010/064395
§ 371 (c)(1),
(2), (4) Date: Jul. 23, 2012

(87) PCT Pub. No.: WO2011/039205
PCT Pub. Date: Apr. 7, 2011

(65) Prior Publication Data
US 2012/0283655 A1 Nov. 8, 2012

(30) Foreign Application Priority Data
Sep. 30, 2009 (EP) .................. 09171738

(51) Int. Cl.
*A61M 5/315* (2006.01)
*A61M 5/24* (2006.01)
*A61M 5/31* (2006.01)

(52) U.S. Cl.
CPC ....... *A61M 5/31585* (2013.01); *A61M 5/3157* (2013.01); *A61M 5/31543* (2013.01);
(Continued)

(58) Field of Classification Search
CPC .... A61M 5/286; A61M 5/282; A61M 5/2425; A61M 5/2429; A61M 5/31586; A61M 5/31543; A61M 5/31585
See application file for complete search history.

(56) References Cited

U.S. PATENT DOCUMENTS 4,973,318 A * 11/1990 Holm et al. .................. 604/208
5,112,317 A * 5/1992 Michel .......................... 604/208
(Continued)

FOREIGN PATENT DOCUMENTS

DE 19900792 6/2000
EP 1923083 5/2008
(Continued)

OTHER PUBLICATIONS

International Preliminary Report on Patentability for International App. No. PCT/EP2010/064395, issued Apr. 3, 2012.
(Continued)

*Primary Examiner* — Bhisma Mehta
*Assistant Examiner* — Matthew A Engel
(74) *Attorney, Agent, or Firm* — McDonnell Boehnen Hulbert & Berghoff LLP

(57) ABSTRACT

A drive member for driving a piston rod in a drug delivery device is provided. The drive member is configured to be driven in a rotational movement by an actuating member. The drive member comprises a track for transmitting a driving load from the actuating member to the drive member. The track comprises both sections running in a distal and
(Continued)

sections running in a proximal direction of the drive member. Moreover, a drug delivery device comprising such a drive member is provided.

11 Claims, 17 Drawing Sheets

(52) U.S. Cl.
CPC ........... *A61M 5/31575* (2013.01); *A61M 5/24* (2013.01); *A61M 5/3146* (2013.01); *A61M 5/31555* (2013.01); *A61M 2005/2407* (2013.01); *A61M 2005/3126* (2013.01); *A61M 2205/581* (2013.01); *A61M 2205/582* (2013.01)

(56) References Cited

U.S. PATENT DOCUMENTS

| | | | |
|---|---|---|---|
| 5,279,585 A * | 1/1994 | Balkwill | 604/207 |
| 5,545,147 A * | 8/1996 | Harris | 604/209 |
| 5,643,214 A * | 7/1997 | Marshall et al. | 604/134 |
| 5,713,857 A * | 2/1998 | Grimard et al. | 604/82 |
| 5,851,197 A * | 12/1998 | Marano et al. | 604/135 |
| 6,068,614 A * | 5/2000 | Kimber et al. | 604/200 |
| 7,094,221 B2 * | 8/2006 | Veasey et al. | 604/187 |
| 7,241,278 B2 * | 7/2007 | Moller | 604/211 |
| 7,427,275 B2 * | 9/2008 | DeRuntz et al. | 604/207 |
| 7,481,977 B2 * | 1/2009 | Percival et al. | 422/64 |
| 7,850,662 B2 * | 12/2010 | Veasey et al. | 604/207 |
| 7,918,833 B2 * | 4/2011 | Veasey et al. | 604/209 |
| 7,935,088 B2 * | 5/2011 | Veasey et al. | 604/207 |
| 7,985,201 B2 * | 7/2011 | Langley et al. | 604/131 |
| 8,257,319 B2 * | 9/2012 | Plumptre | 604/211 |
| 9,358,341 B2 * | 6/2016 | Plumptre | A61M 5/24 |
| 2004/0249348 A1 * | 12/2004 | Wimpenny et al. | 604/207 |
| 2004/0260247 A1 * | 12/2004 | Veasey et al. | 604/207 |
| 2005/0033244 A1 * | 2/2005 | Veasey et al. | 604/211 |
| 2006/0264839 A1 * | 11/2006 | Veasey et al. | 604/209 |
| 2008/0027397 A1 * | 1/2008 | DeRuntz et al. | 604/220 |
| 2009/0198193 A1 * | 8/2009 | Veasey et al. | 604/207 |
| 2009/0264828 A1 * | 10/2009 | Dette et al. | 604/189 |
| 2010/0094205 A1 * | 4/2010 | Boyd et al. | 604/68 |
| 2010/0094206 A1 * | 4/2010 | Boyd et al. | 604/68 |
| 2010/0094207 A1 * | 4/2010 | Boyd et al. | 604/68 |
| 2010/0094253 A1 * | 4/2010 | Boyd et al. | 604/506 |
| 2010/0137792 A1 * | 6/2010 | Boyd et al. | 604/68 |
| 2010/0324494 A1 * | 12/2010 | Plumptre | 604/207 |
| 2010/0324496 A1 * | 12/2010 | Plumptre et al. | 604/207 |
| 2010/0324497 A1 * | 12/2010 | Plumptre | 604/207 |
| 2010/0324527 A1 * | 12/2010 | Plumptre | 604/500 |
| 2010/0331788 A1 * | 12/2010 | Plumptre et al. | 604/207 |
| 2010/0331790 A1 * | 12/2010 | Plumptre | 604/207 |
| 2010/0331791 A1 * | 12/2010 | Plumptre | 604/207 |
| 2010/0331792 A1 * | 12/2010 | Plumptre | 604/207 |
| 2010/0331806 A1 * | 12/2010 | Plumptre et al. | 604/500 |
| 2011/0152784 A1 * | 6/2011 | Veasey et al. | 604/207 |
| 2012/0010575 A1 * | 1/2012 | Jones et al. | 604/211 |
| 2012/0022462 A1 * | 1/2012 | Plumptre | 604/197 |
| 2012/0046643 A1 * | 2/2012 | Plumptre et al. | 604/506 |
| 2012/0089098 A1 * | 4/2012 | Boyd et al. | 604/189 |
| 2012/0089100 A1 * | 4/2012 | Veasey et al. | 604/209 |
| 2012/0283652 A1 * | 11/2012 | MacDonald et al. | 604/211 |
| 2012/0283654 A1 * | 11/2012 | MacDonald et al. | 604/211 |
| 2012/0283658 A1 * | 11/2012 | Plumptre et al. | 604/211 |
| 2012/0283662 A1 * | 11/2012 | MacDonald et al. | 604/236 |
| 2013/0030409 A1 * | 1/2013 | Macdonald et al. | 604/506 |

FOREIGN PATENT DOCUMENTS

| | | |
|---|---|---|
| EP | 1923084 | 5/2008 |
| EP | 1923085 | 5/2008 |
| WO | 2009/080775 | 7/2009 |
| WO | WO 2009/080775 * | 7/2009 |

OTHER PUBLICATIONS

European Search Report for European App. No. 09171738, completed Apr. 6, 2010.
International Search Report for International App. No. PCT/EP2010/064395, completed Apr. 1, 2011.

* cited by examiner

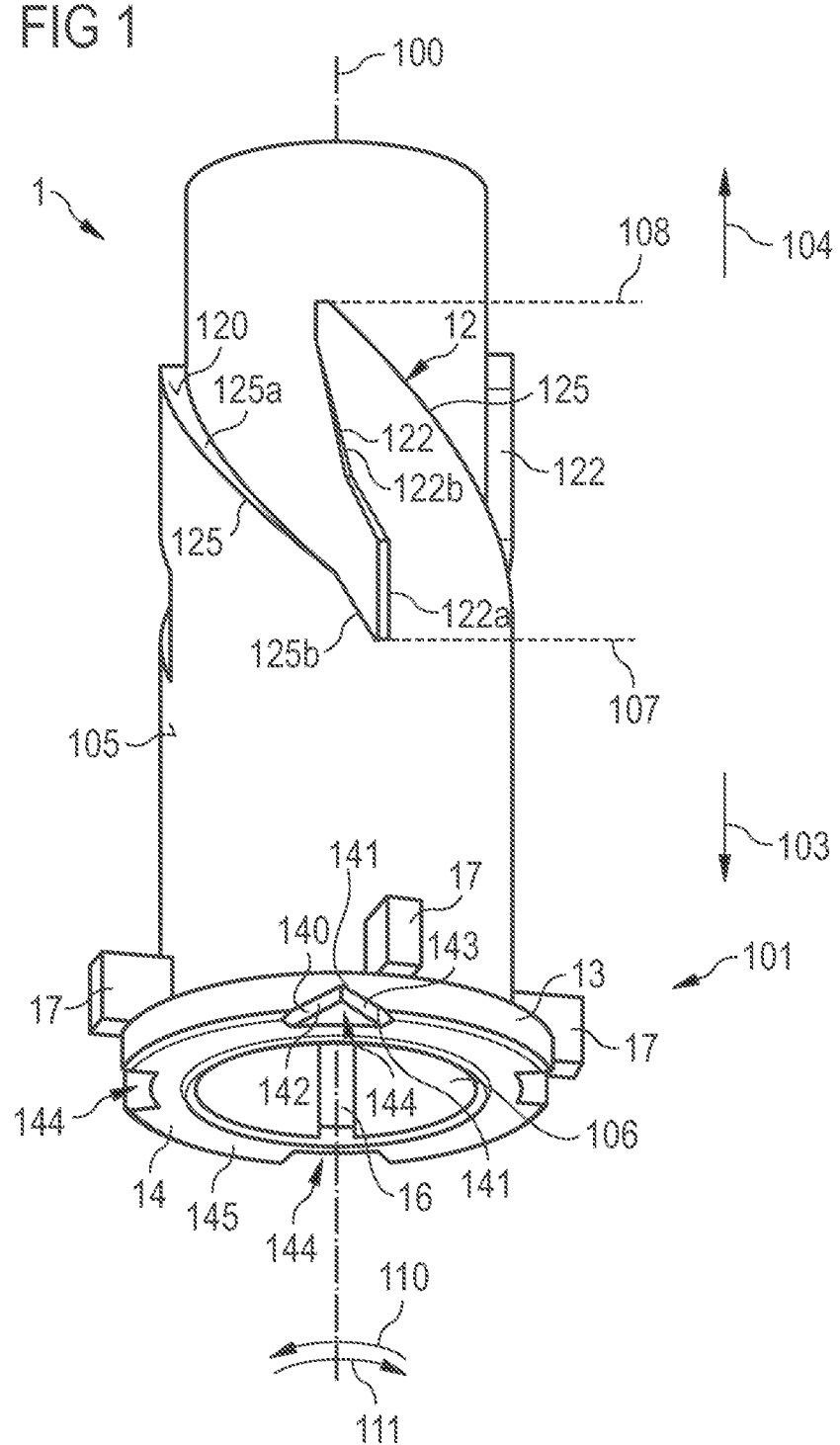

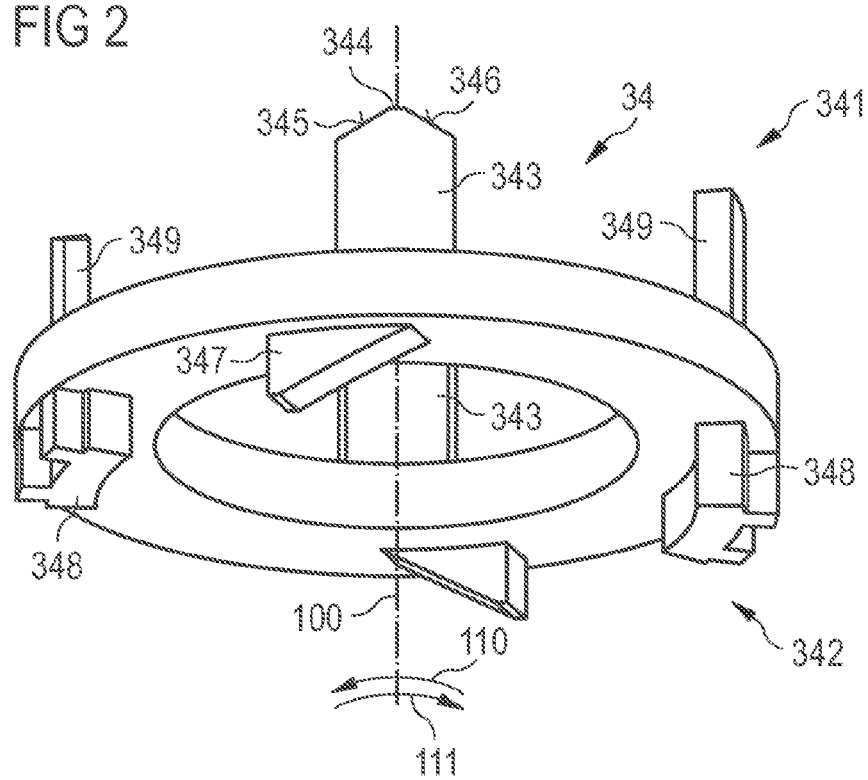
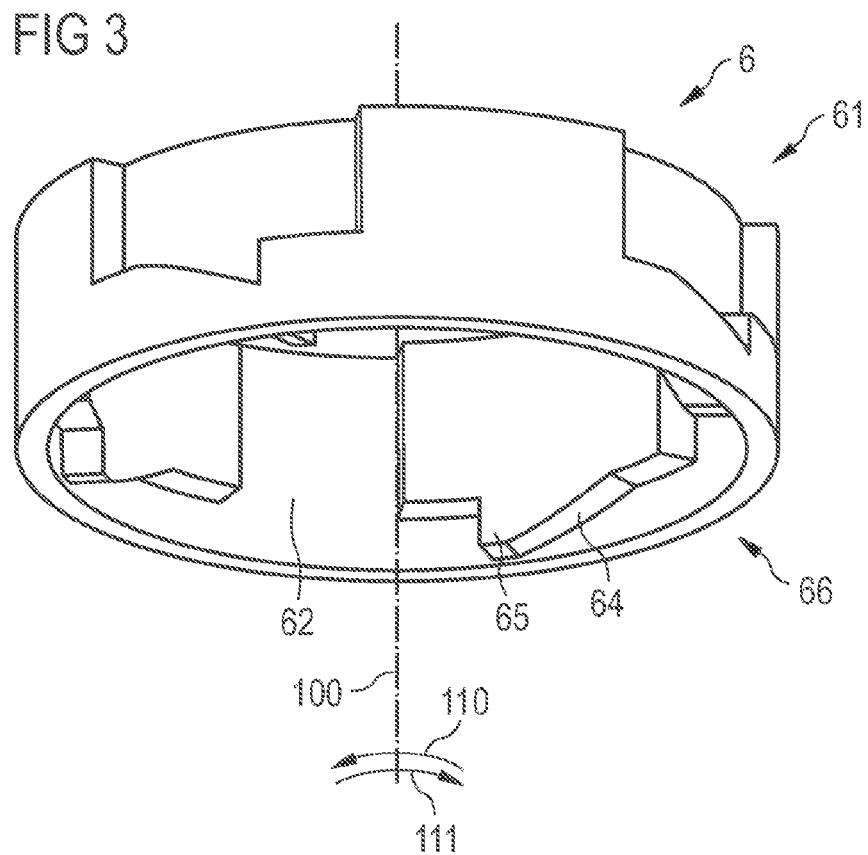

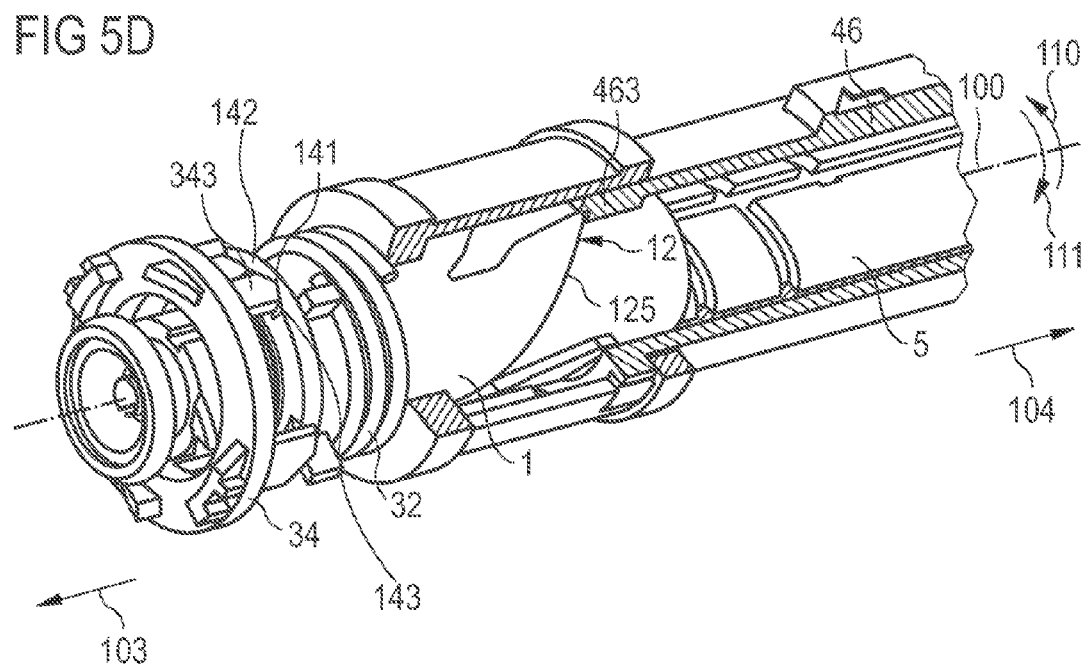

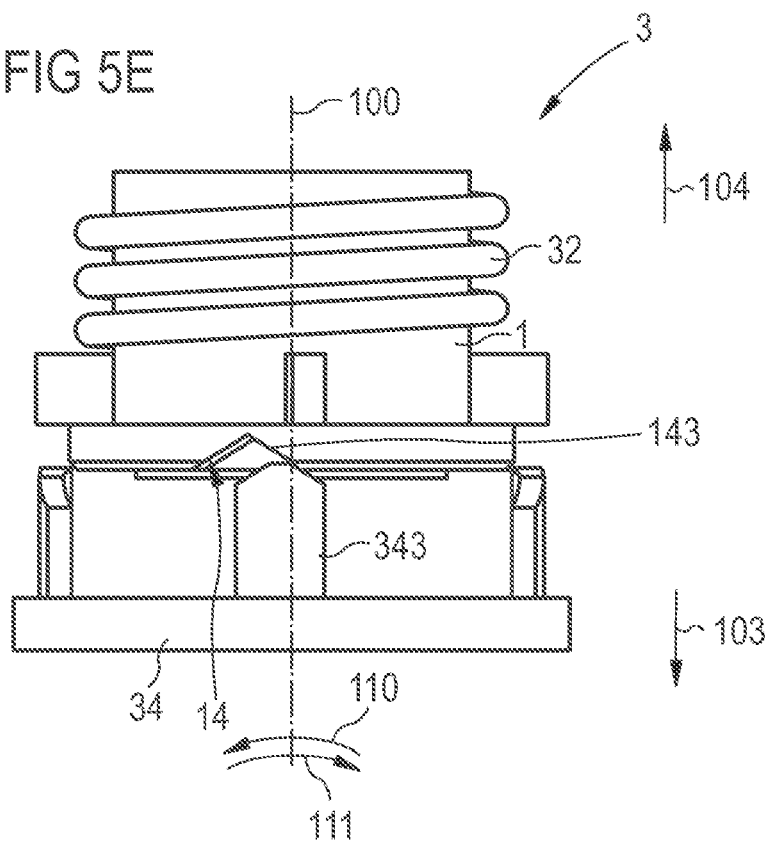
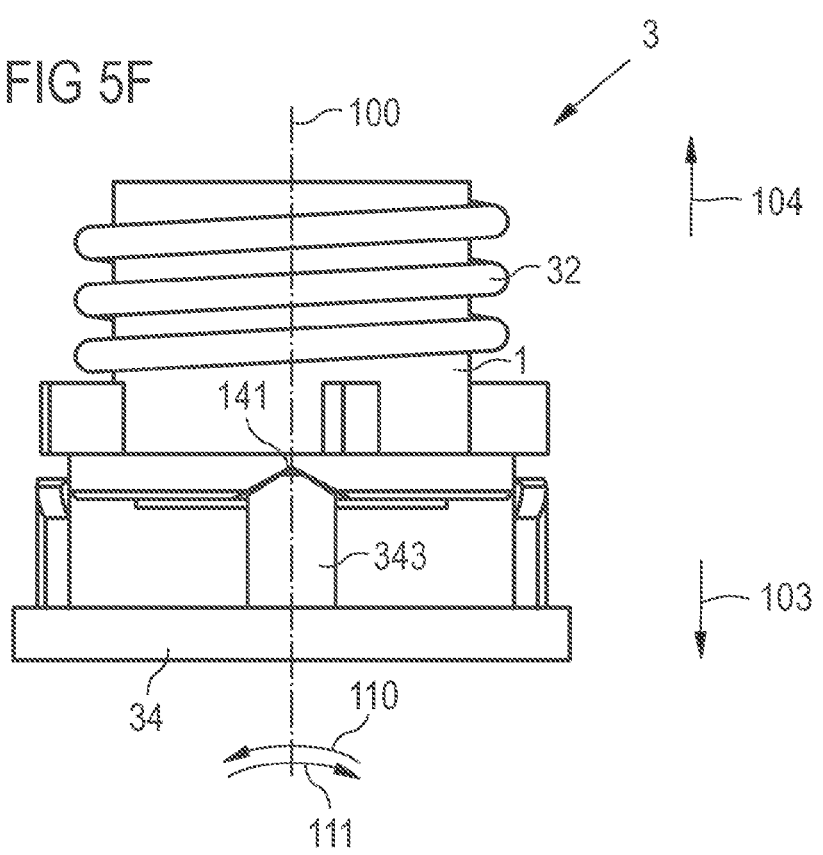

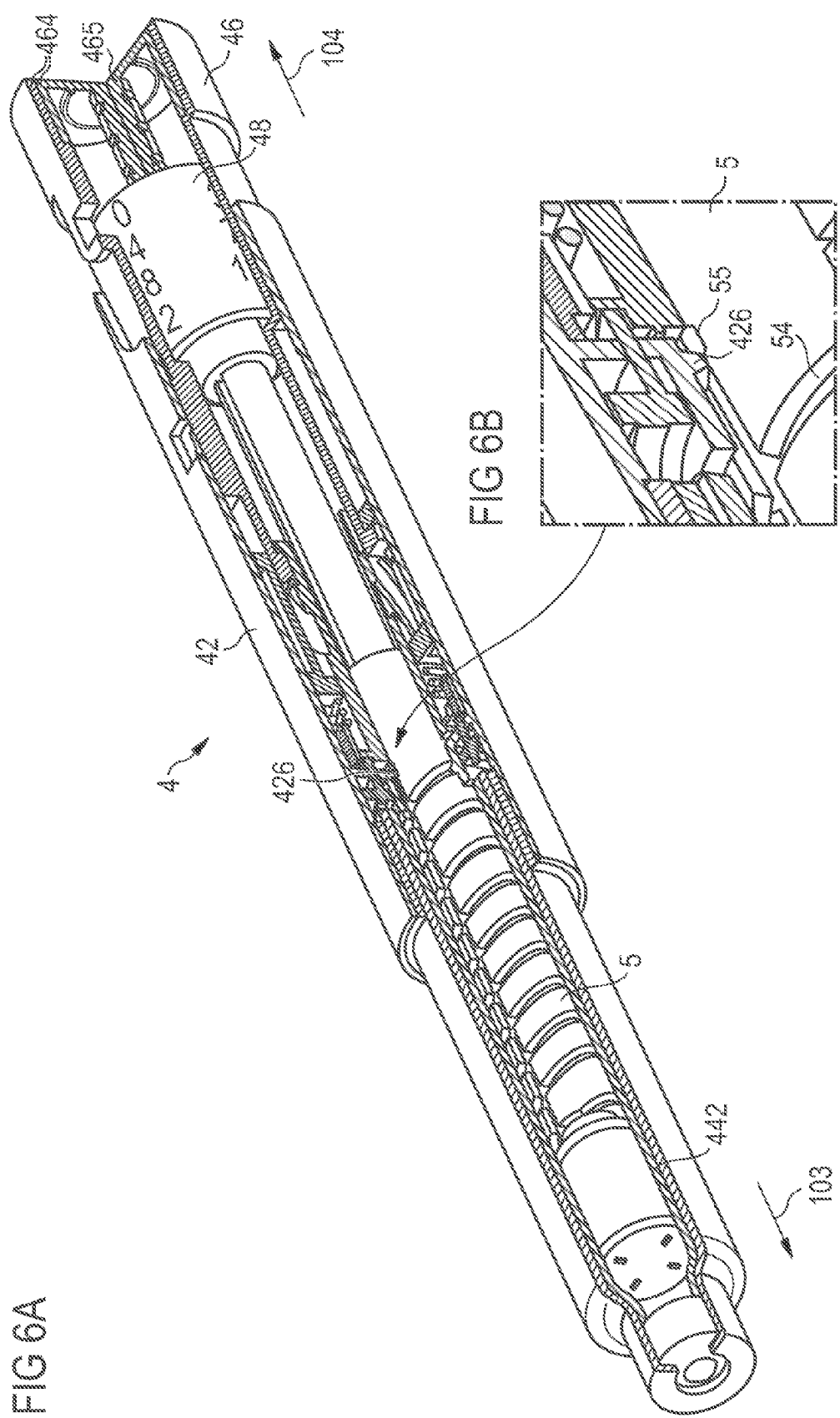

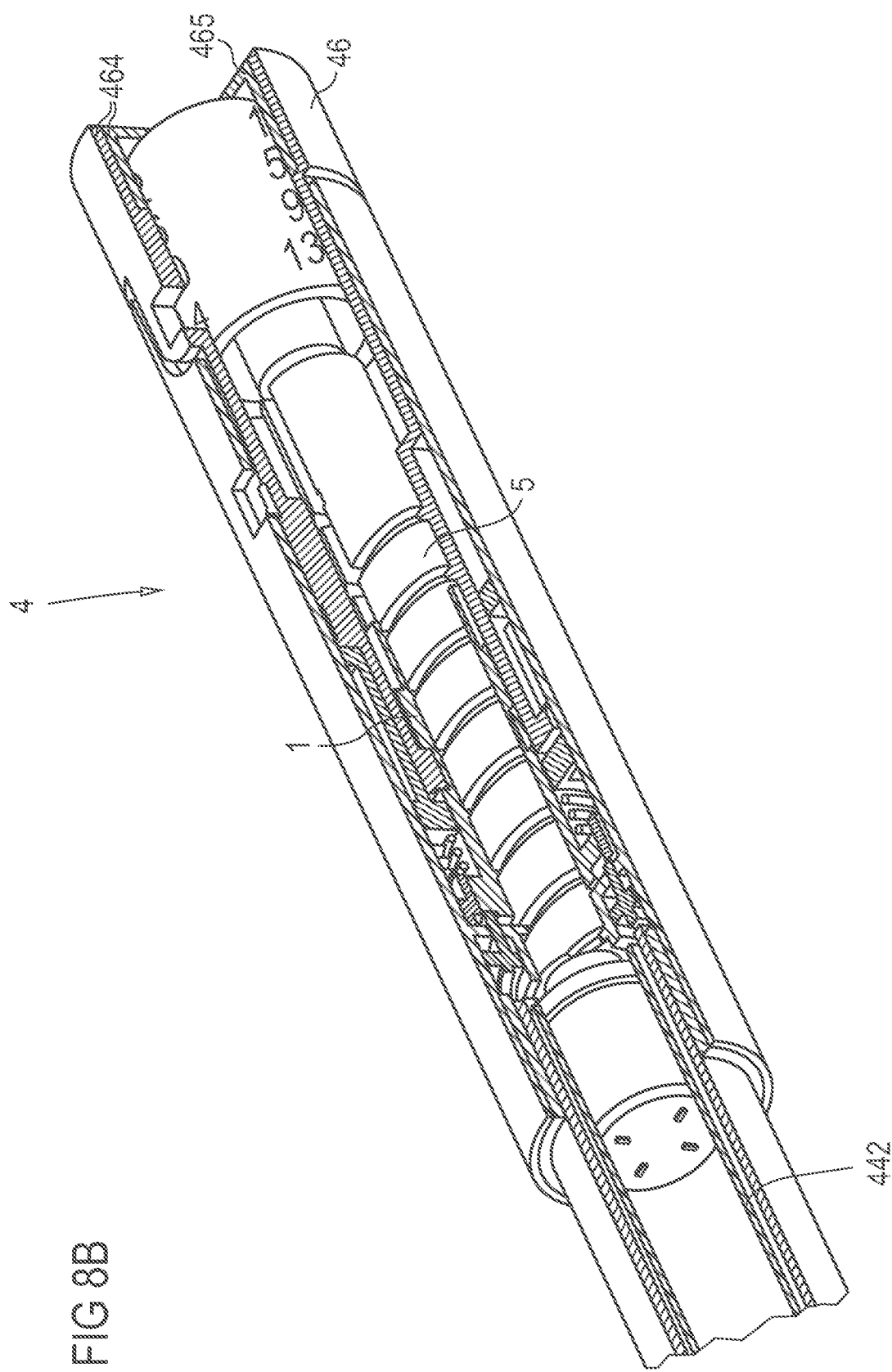

DRUG DELIVERY DEVICE WITH BIASING TRACK FOR TRANSMITTING LOAD TO ROTATABLE DRIVE MEMBER ENABLING SUBSEQUENT DOSE DISPENSE

CROSS REFERENCE TO RELATED APPLICATIONS

The present application is a U.S. National Phase Application pursuant to 35 U.S.C. §371 of International Application No. PCT/EP2010/064395 filed Sep. 29, 2010, which claims priority to European Patent Application No. 09171738.9 filed on Sep. 30, 2009. The entire disclosure contents of these applications are herewith incorporated by reference into the present application.

FIELD OF INVENTION

This disclosure relates to a drive member suitable for use in a drug delivery device for dispensing one or more doses of a drug. Moreover, it relates to a drug delivery device comprising such a drive member for setting and dispensing one or more doses of a drug. The drug delivery device may be a fixed-dose device and may be designed as a pen-type injector.

BACKGROUND

The European patent applications EP 1 923 083 A1, EP 1 923 084 A1, EP 1 923 085 A1 and the international patent application WO 2008/058665 A1 disclose drug delivery devices, wherein a number of pre-set doses of a medicinal product can be administered.

SUMMARY

It is the aim of the present invention to provide a drive member for driving a piston rod in a drug delivery device and a drug delivery device enabling a reliable setting and dispensing of a dose of a medicament.

Structural Characteristics of Drive Member

According to a first aspect of the present invention, a drive member for driving a piston rod in a drug delivery device is disclosed.

Here, the term "piston rod" is used for a component of a drug delivery device, which, by carrying out a movement towards a dispensing end of the drug delivery device, causes medicament to be dispensed from the device. In particular, the piston rod may act on a bung in a medicament container, for example a cartridge, causing medicament to be dispensed from the container. The piston rod may be configured for carrying out a combined axial and rotational movement. As an example, it may be a simple rod or a lead-screw having threads for engaging with corresponding parts of the drug delivery device. The piston rod may be of a unitary or a multi-part construction.

Preferably, the drive member is configured for a direct mechanical interaction with the piston rod. The drive member may comprise coupling means enabling a coupling of a piston rod to the drive member such that a relative translational movement between the drive member and the piston rod is allowed and a relative rotational movement is prevented.

In particular, the drive member may comprise male or female splines configured for being engaged with male or female splines of a piston rod. In further embodiments, the drive member may have a mainly circular cross-section and a flat section differing from the circular cross-sections for engagement with a matching flat section of a piston rod.

The drive member may be particularly suitable for a fixed-dose drug delivery device. Here, the term "fixed-dose" means that in such a drug delivery device a user does not have the option of varying the absolute size of a dose. Preferably, the absolute size of a dose to be dispensed is predetermined by the design of the drive mechanism of the drug delivery device and, in particular, by the design of the drive member.

Preferably, the drive member is configured such that it allows multiple doses of a drug to be subsequently administered. Here, the absolute sizes of the doses may be constant or may vary from dose to dose, depending on the design of the drive member or the drug delivery device.

The drive member may be suitable for being used in a pull-push drug delivery device, wherein by pulling a dose member in a proximal direction of the drug delivery device, a dose of medicament can be set, and by pushing the dose member in a distal direction, the medicament can be dispensed. In this context, setting a dose means that the drug delivery device and, in particular, a drive mechanism of the drug delivery device is prepared for a subsequent dose dispense operation. Preferably, the dose member is directly accessible to a user for setting and dispensing a dose of the medicament. Preferably, in a pull-push device, the dose member carries out a purely axial movement and does not carry out an additional rotational movement. The disclosed drive member may alternatively or additionally be suitable for other drug delivery devices, for example for a push-push device, wherein a dose member is pushed both for setting and dispensing a dose. Preferably, the drug delivery device is an injection device, such as a pen-type device.

Moreover, a drug delivery device suitable to be used with the disclosed drive member may be a disposable or a reusable device. The drug delivery device may be configured such that a cartridge containing a medicament can be mounted in the device. As an example, the cartridge may contain a liquid medicament, for example a GLP-1 or heparin. In a reusable device, an empty cartridge can be replaced by a new cartridge.

The drive member has a longitudinal axis having a distal and a proximal direction. The distal and proximal directions align with the longitudinal axis and are opposite to each other. The drive member may have the shape of a sleeve extending along the longitudinal axis. The sleeve may be configured for at least partially enclosing the piston rod.

Preferably, in an assembled state of a drug delivery device comprising the drive member the distal direction points to the dispensing end of the device. The proximal direction is the direction opposite to the distal direction. In the following, the terms "distal end" and "proximal end" of a component usable in a drug delivery device denote the ends of the component which are reached when moving from the center of the component in the distal or the proximal direction, respectively.

A suitable drug delivery device may comprise a housing, which at least partially encloses the dispense mechanism, for example the drive member, of the drug delivery device. Preferably, the housing has a longitudinal axis being aligned with the longitudinal axis of the drive member. The housing may be configured such that, for example at its distal end, a cartridge holder comprising a cartridge containing a medicament can be attached.

The disclosed drive member may be configured to be driven by an actuating member in a rotational movement around the longitudinal axis. In particular, the drive member may be configured to be driven by an actuating member in a rotational movement around the longitudinal axis both during a dose set and a dose dispense operation.

In one embodiment, the drive member may be configured to be constrained to a purely rotational movement in an assembled state of a drug delivery device. In a further embodiment, the drive member may be configured for additionally carrying out a limited translational movement relative to a housing of the drug delivery device.

Preferably, in an assembled state of a drug delivery device, the actuating member directly acts on the drive member and thereby causes a movement of the drive member, resulting in a movement of the piston rod. The actuating member may be configured to be manually operated by the user. Here, a user may directly act on the actuating member or may act on a component of the drug delivery device which is coupled to the actuating member.

The drive member comprises a track having a contact face for transmitting a driving load from an actuating member to the drive member.

Such a track may be a protruding edge at an outer surface of the drive member. The track may also have other shapes as long as a contact face for transmitting a driving load is provided.

Preferably, the track comprises both sections running in the distal direction and sections running in the proximal direction of the drive member.

This means that, when following the track in one direction relative to the track, at specific sections of the track, the direction of the movement along the track at least partially points into a proximal direction or into a distal direction of the drive member, respectively. Here, pointing in a distal or a proximal direction means that the direction has at least a non-vanishing distal or proximal component, respectively. Preferably, the track runs back and forth between the distal and proximal direction, that means, when following the track, the direction of movement changes several times from a distal to a proximal direction. Preferably, the track has a jagged shape and encircles the longitudinal axis.

In one embodiment, the track is constrained to positions between a first and a second axial position.

In this context, an axial position is defined by a plane crossing the longitudinal axis at a right angle. Thus, running back and forth between the axial positions means that the track is axially constrained to positions between a first and a second plane crossing the longitudinal axis at a right angle.

In further embodiments, for example when the drive member is designed for a drug delivery device where the sizes of subsequent doses differ, the axial positions at which the track changes its direction from a distal to a proximal direction or vice versa may vary along the track. As an example, the track may run from a first axial position in a distal direction towards a second axial position and then again towards the proximal direction but may not reach the first axial position again.

Preferably, the track is closed in itself such that when starting from a specific location on the track and following the track in one direction, the starting location is reached again. In this embodiment, the drive member may be configured such that, in principle, an arbitrary number of doses can be dispensed.

In a preferred embodiment, the track comprises at least one dose set section and at least one dose dispense section, wherein in an assembled form of a drug delivery device, an actuating member acts on the contact face on the dose set section for setting a dose and on the dose dispense section for dispensing a dose.

The dose set section may run in the distal direction and the dose dispense section into the proximal direction of the drive member. Preferably, in an assembled drug delivery device, a contact area between an actuating member and the drive member moves along the track, wherein for setting a dose, the contact area runs in the proximal direction along the dose set section and in the distal direction along the dose dispense section.

In one embodiment, the dose set and dose dispense sections are directly adjacent to each other when following the track in one direction. The track may comprise several dose set and dose dispense sections, wherein every dose set section is followed by a dose dispense section. The dose set sections or the dose dispense sections, respectively, may have identical shapes, only being shifted by a certain angle around the longitudinal axis.

In a preferred embodiment, the track is at least partly configured such that an axial load onto the contact face of the track causes a rotation of the drive member.

For this aim, at least one part of the dose dispense section may be inclined relative to the longitudinal axis with an absolute size of the inclination angle larger than 0° and smaller than 90°. Thereby, an axial load is at least partially redirected into a torque around the longitudinal axis of the drive member. Accordingly, the drive member may be configured such that an actuating member constrained to an axial movement relative to the drive member may cause a rotational movement of the drive member. Preferably, here, the contact face is directed to the proximal direction of the drive member, such that a load directed to the distal direction can be applied on the drive member. Also in this context, the term "directed to the proximal direction" means that the direction has at least a non-vanishing component directed to the proximal direction.

The inclination angle of the track relative to the longitudinal axis affects the velocity ratio and, subsequently, the mechanical advantage of the drug delivery device. The velocity ratio can be defined by the amount of axial movement of an actuating member operated by a user in a dose dispense operation compared to the amount of axial movement of a piston rod. The mechanical advantage can be defined as the ratio of user input force to output force on the bung. The velocity ratio increases when the inclination angle of the track decreases. This increase in the velocity ratio results in an increase in the mechanical advantage of the device. Generally, the mechanical advantage will be less than the velocity ratio because of the effects of friction losses.

The dose dispense section may comprise parts differing in their inclination angles. Thereby, at certain phases of a dose dispense operation the mechanical advantage can be adjusted to a desired course. In particular, in a phase of the dose dispense operation, where the drive member acts on further components of the drug delivery device, a larger force would be needed for actuating the drive member. Here, the force applied by a user can be kept constant by adjusting the inclination angle.

In one embodiment, the dose set section comprises at least one part being inclined to the longitudinal axis. Preferably, here, the contact face is directed to the distal direction of the drive member, such that a load directed to the proximal direction can be applied on the drive member.

Preferably, in the case that the drive member is configured such that an actuating member causes a rotation of the drive member during both a set and dispense operation, the rotation during a dose dispense operation is directed in a first rotational direction and during a dose set operation in a second rotational direction opposite to the first rotational direction.

The track may be configured such that not all parts of a dose dispense or a dose set section are inclined to the longitudinal axis. In particular, the dose set or the dose dispense section may have parts being parallel to the longitudinal axis.

In one embodiment, the drive member comprises a bias track having a contact face for transmitting a load from a component of a biasing means to the drive member. Thereby, the drive member is biased towards a rotation around the longitudinal axis. In particular, the biasing means may thereby exert a torque on the drive member.

The bias track may be located at the distal end of the drive member. As an example, the bias track may be located at the front face of the drive member. The bias track may follow a circumferential line of the drive member and may be closed in itself.

In one embodiment, the load exerted by the component of the biasing means on the contact face may be an axial load which is redirected into a torque or a combined axial load and a torque by the interaction of the component of the biasing means and the bias track. In an assembled state of a drug delivery device, the component of the biasing means may be fixed to a housing during dose setting and dose dispensing, while the drive member carries out a rotational movement relative to the housing.

The biasing means may further comprise a spring, wherein by a tensioning of the spring, a load is created between the component of the biasing means and the drive member. The spring may be located on the drive member.

The bias track may comprise at least one first redirecting section being inclined to the longitudinal axis. Preferably, the absolute size of the angle of inclination of the first section and the longitudinal axis is larger than 0° and smaller than 90°.

The bias track may additionally comprise at least one second redirecting section. In one embodiment, the second redirecting section is inclined to the longitudinal axis in a sense opposite to the first redirecting section.

The inclination of the bias track enables an axial load on the drive member to be redirected into a torque, wherein the direction of the torque is determined by the sense of inclination.

In a preferred embodiment, the first and the second sections are adjacent to each other, thereby forming a recess in the track. The recess may be a triangular recess having the first and second sections as its side faces and a center point between the first and second sections.

Structural Characteristics of Drug Delivery Device Comprising the Drive Member

According to a further aspect of the present disclosure, a drug delivery device is provided, which is configured to dispense a dose of a drug in a dose dispense operation as well as being configured to prepare the device for a subsequent dose dispense operation in a dose set operation. The drug delivery device has a drive member for driving a piston rod as described above.

A suitable drug delivery device may be a single- or a multi-dose device and may be disposable or reusable. Preferably, the drug delivery device is a fixed-dose device.

The drug delivery device may be manually operable by a user through a dose member such that the user supplies the force needed for driving the drive member. Preferably, the dose member is directly accessible to a user.

As an example, the dose member may comprise a dose button at a proximal end of a drug delivery device which can be pulled out of a housing for setting a dose and pushed towards the housing for dispensing a dose.

The dose member may serve as the actuating member for driving the drive member. Here, the actuating member may be fixed to the dose member or may be an integral part of the dose member. In a different embodiment, the actuating member may be coupled to the dose member such that the movement of the dose member is transferred to the actuating member during a dose set and a dose dispense operation.

In a different embodiment, the drug delivery device may be configured such that the force for driving the drive member is partially or fully supplied by a mechanism of the drug delivery device. Here, a user may only trigger a dose dispense or dose set operation.

In one embodiment, the device comprises biasing means configured to bias the drive member at one of or both the end of a dose set operation and a dose dispense operation towards a rotation around the longitudinal axis. Preferably, at the end of the dose set or the dose dispense operation the bias is released by the drive member following the torque and thereby carrying out a small rotation.

The bias may be created during the respective dose set or dose dispense operation. In particular, a torque may be created by a mechanical interaction of a component of biasing means and a contact face of a bias track at the drive member as described above. In different embodiments, a torque may be created by a torsion spring tensioned by a rotational movement of the drive member during a dose set or dispense operation.

Moreover, the drug delivery device comprises an actuating member for driving the drive member in a rotational movement around the longitudinal axis.

The actuating member acts on the contact face of the track, thereby transmitting a driving load onto the drive member. As an example, the actuating member may have a lug for acting on the drive member. The lug may have a curved shape such that, depending on the direction of the contact face, a load in a distal or proximal direction can be applied on the drive member. Preferably, a contact area of the actuating member and the drive member at which the load is transmitted from the actuating member onto the drive member runs along the track during dose setting and dispensing.

In a preferred embodiment, at the end of dose set operation, the torque exerted by the biasing means results in a rotation of the drive member towards a position relative to the actuating member such that a subsequent dose dispense operation is enabled.

As an example, the dose set section of the track may run in the proximal direction towards a peak. At the peak, the track changes its direction from the proximal direction to the distal direction. After the peak, the dose dispense section starts, running into the distal direction. In a dose set operation, the contact area between the drive member and the actuating member moves along the dose set section until the peak is reached. In order to enable the contact area to pass the peak and thus, enable a contacting of the actuating member on the dose dispense section, the drive member may carry out a small rotation relative to the actuating member.

This may be particularly useful when the dose member is constrained to an axial movement along the longitudinal axis of the drive member. As an example, the dose member may be configured for being pulled for setting a dose and being pushed for dispensing the set dose. In a different embodiment, the dose member may be configured for both being pushed for setting and dispensing a dose.

Preferably, the drug delivery device comprises a piston rod configured to be driven by the drive member in a dose dispense operation of the drug delivery device. Preferably, a relative rotational movement between the piston rod and the drive member is prevented and a relative axial movement is enabled.

Here, the drive member may comprise suitable coupling means for coupling the piston rod as described above. In particular, the piston rod and the drive member may be coupled by a splined engagement.

In one embodiment, at the end of a dose dispense operation, the torque exerted by the biasing means results in a rotation of the drive member such that the piston rod is moved in the proximal direction. Thereby, a relaxation of a bung in a cartridge towards the proximal direction of the drug delivery device may be enabled. This may help to reduce a dripping of medicament out of the cartridge.

Preferably, here, the bias is directed towards a second rotational direction opposite to the first rotational direction.

In one embodiment, the drug delivery device comprises a threaded component being fixed to the housing of the drug delivery device. The threaded component is threadedly engaged with the piston rod.

In particular, the threaded component may have the shape of a sleeve and may be located at an inner surface of the housing. At its inner surface, the threaded component may comprise a thread engaged with a thread on the outer surface of the piston rod.

As the piston rod is coupled to the drive member such that it follows a rotational movement of the drive member, its threaded engagement leads to a combined translational and rotational movement relative to the housing of the drug delivery device. Depending on the direction of rotation of the drive member, the piston rod carries out a movement either in the distal or the proximal direction of the drug delivery device. During a movement in the distal direction, the piston rod may act on a bung in a cartridge, whereby a medicament is dispensed. A movement in the proximal direction may be caused for allowing a relaxation of the bung.

In one embodiment, the drug delivery device comprises a dose counter for displaying at least one of the number of remaining doses of the drug and the number of administered doses of the drug.

Thereby, a user may be informed on the number of doses left in a medicament container, for example a cartridge, and thus, on the number of remaining drug dispense operations.

As an example, the dose counter may have the shape of a sleeve, carrying markings on its outer surface. The markings may be arranged on a helical circumference of the dose counter. Each marking may indicate a number of remaining doses. The marking corresponding to the present filling state of the medicament container may be visible through a display window, which may be an opening of a housing of the drug delivery device. In further embodiments, depending on the design of the drug delivery device, the marking may be visible through an opening of the dose member.

The dose counter may be threadedly engaged with the housing or a component fixed to the housing.

In one embodiment, the dose counter is driven by the drive member. Here, the drive member and the dose counter may be coupled to each other such that a relative translational movement of the drive member and the dose counter is allowed and a relative rotational movement is prevented. As an example, the drive member and the dose counter may have a splined engagement. By the rotational coupling of the dose counter to the drive member and the threaded engagement with the housing, a rotational movement of the drive member causes a combined translational and rotational movement of the dose counter relative to the housing.

Preferably, in this embodiment, the drive member is in a splined engagement with the piston rod. In this case, the amount of rotational movement of the drive member equals the amount of rotational movement of the piston rod. This enables a sufficiently accurate adjustment of the dose counter by utilizing the movement of the drive member such that the displayed number of doses accurately corresponds to the position of the piston rod.

In a further embodiment, the dose counter may be driven by the piston rod. Also here, the dose counter may be coupled to the piston rod such that a relative translational movement of the piston rod and the dose counter is allowed and a relative rotational movement is prevented. Also here, by the rotational coupling of the dose counter to the piston rod and the threaded engagement with the housing, a rotational movement of the drive member causes a combined translational and rotational movement of the dose counter relative to the housing.

Functional Characteristics of Drug Delivery Devices

In a further aspect of the present disclosure, a drug delivery device for dispensing one or more doses of a drug is provided. The device comprises a drive member for driving a piston rod in a dispense action of the drug delivery device and a dose member for actuating the drive member. The piston rod is coupled to the drive member such that a relative translational movement of the drive member and the piston rod is allowed and a relative rotational movement is prevented. The drive member is configured to be driven by the dose member in a first and a second rotational direction around the longitudinal axis, wherein the first and second rotational directions are opposite to each other.

The drive member may have stable and unstable states relative to a longitudinal axis of the drug delivery device, wherein in an unstable state the drive member is biased by a biasing means towards a stable state. Preferably, in an unstable state, the drive member is biased towards a rotation around the longitudinal axis and in a stable state the drive member is unbiased towards any rotation around the longitudinal axis. In particular, in an unstable state, the biasing means may exert a torque on the drive member. In a stable state, the biasing means may not exert a torque on the drive member and, thereby, the drive member may be free from a torque.

In a further aspect of the present disclosure, a drug delivery device for dispensing one or more doses of a drug comprises a drive member for driving a piston rod in a dispense operation of the drug delivery device. Furthermore, the drug delivery device comprises a dose member for actuating the drive member. The drive member has stable and unstable states relative to the longitudinal axis. In an unstable state, the drive member is biased by biasing means towards a stable state. Preferably, in an unstable state, the drive member is biased towards a rotation around the longitudinal axis and in a stable state the drive member is unbiased towards any rotation around the longitudinal axis.

In the following, further characteristics of drug delivery devices are described which are equally applicable to the embodiments of drug delivery devices according to the aspects of the disclosure given above.

Moreover, the drug delivery devices may comprise any feature or combination of features described in this disclosure. In particular, the drive member may have the structural characteristics of the drive member as described above. However, the drug delivery device is not restricted to such a drive member.

The dose member may be operable by a user. In particular, the dose member may comprise a dose button accessible to a user. The dose member may be constrained to an axial movement along a longitudinal axis of the device for setting and dispensing a dose of medicament. In particular, the dose member may be configured to be pulled in a proximal direction of the drug delivery device for setting a dose and to be pushed in a distal direction of the drug delivery device for dispensing the dose.

Preferably, the drug delivery device is designed such that a movement of the drive member in a first and a second rotational direction results in an axial movement of the piston rod. Here, a rotation in the first rotational direction of the drive member may result in a distal movement of the piston rod. The movement in the second rotational direction may result in a movement of the piston rod in the proximal direction.

Preferably, the unstable and stable states exist at predefined phases of a dose set or dispense operation. Here, the dose set or dispense operations may be associated with relative angular positions of the drive member and a housing such that the unstable and stable states exist at predefined relative angular positions of the drive member and the housing.

Preferably, an unstable state is created during one of or both a dose set and dose dispense operation. Preferably, at the end of a dose set or dose dispense operation the bias causes a small rotation of the drive member. Thereby, after a dose dispense operation, a backing-off of the piston rod may be achieved. After a dose set operation, a small rotation may result in a small relative rotation of the drive member and the dose member, enabling a subsequent dose dispense operation.

The stable and unstable states may be created by an interaction of a component of biasing means and a bias track on the drive member.

The biasing means may comprise a spring. In particular, the spring may be a torsion spring exerting a torque on the drive member. In a different embodiment, the spring may be a compression spring. Such a compression spring may exert an axial load between a further component of the biasing means and the drive member.

In one embodiment, the biasing means comprise redirecting means for redirecting a load in an axial direction into a load in a rotational direction around the longitudinal axis.

Such redirecting means may be provided by inclined sections of a bias track on the drive member. In particular, the redirecting means may comprise a contact surface being inclined to the longitudinal axis, wherein the absolute size of the angle of inclination is larger than 0° and smaller than 90° relative to the longitudinal axis.

The biasing means may be configured to bias the drive member at the end of a dose set operation towards the first rotational direction relative to the longitudinal axis.

Preferably, at the end of a dose set operation, such a torque exerted by the biasing means results in a rotation of the drive member.

Additionally or alternatively, the biasing means may be configured to bias the drive member towards the second rotational direction relative to the longitudinal axis at the end of a dose dispense operation.

Preferably, at the end of a dose dispense operation, such a torque exerted by the biasing means results in a rotation of the drive member. Preferably, the piston rod is coupled to the drive member and the housing such that a rotation of the drive member results in a translational movement of the piston rod relative to the housing. Here, the coupling may also result in a combined rotational and translational movement. Preferably, at the end of a dose dispense operation, the rotation of the drive member causes a movement of the piston rod in the proximal direction of the housing. Thereby, a relaxation of a bung in a cartridge in the proximal direction may be enabled.

Preferably, in the case that the biasing means are configured for biasing the drive member in both a first and a second rotational direction, the first and the second rotational directions are opposite to each other.

Preferably, on a small deflection of the drive member from the stable state, a bias is created back towards the stable state.

As an example, a stable state may be accomplished by an engagement of a component of biasing means at a center of a recess at a bias track. Such a component acting on the bias track of the drive member may have the shape of a ring, wherein the central axis of the ring aligns with the longitudinal axis of the drive member and the longitudinal axis of the drug delivery device. The component may comprise one or more bias lugs contacting the bias track. Preferably, both side faces of the recess are inclined relative to a longitudinal axis of the drive member such that on a small relative deflection of the component from the center of the recess towards any of the side faces, a backwards force towards the center of the recess arises. Preferably, the backwards force leads to a rotation of the drive member until the lugs of the component are re-located at the center of the recess.

By providing stable states, a well-defined small rotation of the drive member relative to the housing can be achieved. In particular, an over-travel of the drive member relative to the housing can be prevented.

Moreover, the drive member may comprise a neutral state being configured such that on a small deflection from the neutral state, the drive member is one of biased towards a stable state and unbiased towards any rotational state.

Such a neutral state of the drive member may be accomplished by an interaction of a bias track on the drive member and a component of biasing means on a part of the bias track being perpendicular to the longitudinal axis of the drive member. In this case, an axial load between the drive member and the component of biasing means does not result in a torque on the drive member. The drive member may be in the neutral state in certain operation phases of the dose set and dose dispense operations.

In one embodiment, the drive member is configured such that in an unstable state, the torque exerted by the biasing means results in a rotation towards a stable state of the drive member, in the case that the rotation of the drive member is unhampered by the dose member.

In particular, during a dose set or dose dispense operation the bias created by the biasing means may be balanced by a counterforce exerted by the dose member on a contact face of a track on the drive member. As an example, in the case that the dose member is operated by a user, the user may release the dose member after a dose dispense operation. Thereby, the counterforce exerted by the dose member on the drive member is removed such that a rotation of the drive member caused by the bias is enabled. Here, a rotation of the drive member may cause a movement of the dose member in the proximal direction of the drug delivery device.

Additionally or alternatively, at the end of a dose set operation, the dose member may come out of contact with a contact face of a track on the drive member such that the counterforce is removed and a relative rotation of the drive member to the dose member and the housing is enabled. In this case, it may not be necessary to release the dose member at the end of a dose set operation for allowing a small rotation of the drive member.

Functional Characteristics of a Resettable Drug Delivery Device

Moreover, a resettable drug delivery device for dispensing one or more doses of a drug is disclosed. The drug delivery device comprises a piston rod having a start position relative to the housing and being resettable to the start position. Furthermore, the drug delivery device comprises a drive member for driving the piston rod in a dispense operation of the drug delivery device in a distal direction of the drug delivery device. Moreover, the drug delivery device comprises a dose member for actuating the drive member. The drug delivery device is configured such that during resetting the drug delivery device, the dose member is in a pulled-out position relative to the housing. In this context, the specification "during resetting" means that at least at one point of time during the resetting operation, the dose member is in the pulled-out position.

In particular, the drug delivery device may have a reset state, wherein in the reset state a resetting of the device and in particular a resetting of the piston rod is enabled. Preferably, the dose member is in a pulled-out position relative to the housing during the reset state of the device. Moreover, the drug delivery device may have a dispense state, wherein in the dispense state a dose setting and dispensing is enabled. The drug delivery device may be configured to be switched from the dispense state in the reset state.

The dose member may be operable by a user. Preferably, the dose member is directly accessible to a user. By actuating the dose member a dose setting or dispensing of the medicament may be initiated. In particular, the dose member may comprise a dose button accessible to a user. Preferably, the dose button is fixed to the dose member or is an integral part of the dose member such that a movement of the dose button results in a movement of the dose member. The dose button may be located at the proximal end of the drug delivery device. In a pulled-out position, the dose button and therewith the dose member may be in its most proximal position relative to the housing. In a pushed-in position, the dose button and therewith also the dose member may be in its most distal position relative to the housing. For setting and dispensing a dose, the dose member may be constrained to an axial movement along the longitudinal axis between the pushed-in and pulled-out position.

The resettable drug delivery device may comprise any feature or combination of features described in this disclosure. In particular, the drive member may have the structural characteristics of the drive member as described above. However, the drug delivery device is not restricted to such a drive member.

In a preferred embodiment, the piston rod is coupled to the drive member such that for resetting the piston rod to its start position, a free rotation of the drive member has to be enabled. In particular, the piston rod may be coupled to the drive member such that a translational movement between the piston rod and the drive member is allowed while a rotational movement is prevented. Furthermore, the piston rod may have a threaded engagement with the housing. Thus, during resetting, the piston rod may carry out a combined rotational and translational movement relative to the housing.

Preferably, the drug delivery device is a reusable device, allowing for a medicament container, for example a cartridge, to be replaced. Preferably, the device is configured such that a resetting of the device is enabled in any filling state of the cartridge. In particular, a resetting is enabled also when the cartridge is not fully emptied.

In particular, the drug delivery device may comprise a main housing to which a cartridge holder containing a medicament cartridge can be releasably attached. In an assembled state of the drug delivery device, the cartridge holder is attached to the housing and in an unassembled state the cartridge holder is detached from the housing.

Preferably, the drug delivery device is configured such that after removing the cartridge holder from the housing, the piston rod is movable to the start position.

Here, by removing the cartridge holder from the housing, the piston rod may be accessible such that a load for resetting the piston rod can be applied on the piston rod. Additionally or alternatively, by removing the cartridge holder, parts of the drive mechanism or other parts of the drug delivery device may be decoupled, thereby allowing a movement of the piston rod in the proximal direction.

Thereby, the drug delivery device may be switched from the dispense state in the reset state.

The drug delivery device may be configured such that in the unassembled state, the piston rod is movable towards the start position by exerting an axial load on the piston rod in a proximal direction of the drug delivery device.

The axial load may be supplied by a user, for example by manually pushing the piston rod backwards. Here, the user may apply the load onto the distal end of the piston rod or onto a bearing at the distal end of the piston rod. In a further embodiment, an axial load may be exerted by a cartridge or a part of the cartridge holder when attaching the cartridge holder to the housing of the drug delivery device. In the case that, during resetting, the piston rod carries out a combined translational and rotational movement, the piston rod may also be moved to the start position by rotating the piston rod.

In one embodiment, the drug delivery device is configured such that, in the unassembled state, the piston rod moves towards the start position by orienting the drug delivery device such that the distal direction points upwards.

In this case, the friction of the drive mechanism of the drug delivery device has to be sufficiently small such that a movement of the piston rod through its own weight is enabled. Here, on an upwards orientation of the drug delivery device, also the dose member may move towards the pulled-out position by itself.

In one embodiment, the drug delivery device may be configured such that the dose member is in the pulled-out position already before resetting the piston rod.

In this case, the dispense mechanism of the drug delivery device may be configured such that after the last available has been dispensed, a subsequent dose set operation may be allowed. In particular, for setting a dose, the dose member may be pulled out of the housing of the drug delivery device and thus, may be moved into the pulled-out position. The dispense mechanism may be configured such that a subsequent movement of the dose member and, here, in particular, pushing the dose member back towards the housing, e. g. for dispensing a further dose, is blocked. For this aim, the piston rod may comprise a thread being engaged with a component fixed to the housing. At its proximal end, the thread may have a stop face, preventing a further movement of the piston rod relative to the component towards a distal direction after the last available dose has been dispensed. Thereby, also a further movement of the dose member in the distal direction may be blocked.

In a further embodiment, the resettable drug delivery device is configured such that the dose member is moved towards the pulled-out position during resetting the piston rod.

Here, the piston rod may be coupled to a drive member such that a relative rotational movement of the piston rod and the drive member is prevented and a relative translational movement is allowed. As an example, the piston rod may have a splined engagement with the drive member. Thus, a movement of the piston rod towards the proximal end of the drug delivery device causes a rotation of the drive member. The drive member may be coupled to the dose member such that a rotation of the drive member results in an axial movement of the dose member. As an example, the drive member may have an inclined contact face for transmitting a load from the dose member onto the drive member for a set and dispense operation of the device. By a rotation of the drive member the contact face may act on the dose member such that the dose member is pushed in the proximal direction.

In a preferred embodiment, the drug delivery device is configured such that the dose member is in its pulled-out position after resetting the piston rod. This may indicate that the drug delivery device is ready for a priming operation.

In this context, the term "priming" may mean that relative displacements of parts of the drive mechanism towards each other due to the resetting operation are compensated. In particular, in order to prime the device after resetting the device and after a new medicament container has been inserted, the dispense mechanism may be actuated such that the gaps between the different parts of the dispense mechanism are removed. By removing these gaps, an accurate setting and dispensing of the first dose is enabled after the drug delivery device has been reset.

Preferably, when the dose member is in the pulled-out position, priming may be accomplished by pushing the dose member towards the housing. Thereby, the drive mechanism may carry out a priming operation being similar to a dose dispense operation. Here, depending on the size of the gaps between the different parts of the drive mechanism, a small dose may be dispensed from the drug delivery device. After priming, the drug delivery device is ready for use.

In its assembled state, the drug delivery device may comprise resilient means exerting a load on the housing or a component coupled to the housing and the drive member towards each other.

In particular, the component may be a part of biasing means exerting a bias on the drive member. As an example, the drive member may have a bias track contacted by a component of biasing means. The component of the biasing means and the drive member may be pushed towards each other by a resilient means in form of a spring. Thereby, the friction of the drive mechanism is increased and accordingly, a higher force is needed for moving the drive member relative to the housing. This may prevent a backwards movement of the piston rod in an assembled state when the drug delivery device is oriented upwards.

Preferably, the drug delivery device is configured such that the load is released on removal of the cartridge holder.

As an example, in its assembled state, the cartridge holder may exert a load on parts of the drug delivery device and the resilient means such that the resilient means is tensioned and the parts are pressed together. As an example, the cartridge holder may push a component of biasing means towards the drive member and thereby compress a spring exerting a counterforce on the drive member and the component of biasing means.

When the cartridge is detached from the housing of the drug delivery device, the load may be removed, whereby the spring is allowed to relax. This may enable a decoupling of parts of the drug delivery device. In particular, a component of biasing means may be decoupled from the drive member, whereby a rotation of the drive member is facilitated. Thereby, also the resetting of the piston rod may be facilitated. Depending on the amount of friction after the detachment of the cartridge holder, the piston rod may be pushed towards its start position or may move on its own towards the start position when the drug delivery device is pointed upwards.

In one embodiment of the resettable drug delivery device, the dose member may be coupled to the drive member such that when the dose member is retained in a pushed-in position relative to the housing, the dose member obstructs the free orientation of the drive member relative to the housing.

As an example, the dose member may be coupled to the drive member such that in a pushed-in position a limited rotation of the drive member relative to the housing is allowed, whereas a free rotation enabling a resetting of the piston rod towards a start position is prevented. Here, in particular, a relative rotation of the drive member and the housing may be prevented at certain relative angular positions of the drive member and the housing. As an example, the drive member may comprise a track for transmitting a load from the dose member towards the drive member in a dose set and dispense operation. In the case that the track at least partially runs in a distal or a proximal direction of the longitudinal axis of the drug delivery device and is in contact with the dose member, a rotation of the drive member relative to the dose member may result in an abutment of the contact face of the track with the dose member, preventing a free rotation of the drive member. In the case that the dose member is constrained to an axial movement relative to the housing, this implies that also a free rotation of the drive member relative to the housing is prevented as long as the dose member remains in its pushed-in position. Here, the dose member may obstruct a free rotation until it is moved in a pulled-out position, where its contact to the contact face is lost.

Furthermore, the drug delivery device may comprise a unidirectional element coupling the drive member to the housing such that in an assembled state of the drug delivery device a relative rotational movement of the drive member and the housing is allowed in one rotational direction and a relative rotational movement in a second rotational direction is prevented at certain relative angular positions of the housing and the drive member.

As an example, such a unidirectional element may be a feedback element for providing audible or tactile feedback to a user at certain phases of a dose dispense or dose set operation. In particular, the feedback element may indicate that a dose set or dose dispense operation has been completed.

Preferably, in an assembled state, the resilient means exert a load onto the unidirectional element and a component fixed to the housing towards each other.

Thereby, a unidirectional coupling between the drive member and the housing may be provided such that in the assembled state a free relative rotational movement of the drive member and the housing may be prevented. Preferably, by removing the cartridge holder from the housing, the resilient means is allowed to relax such that the load between the unidirectional element and a component fixed to the housing is removed. Thereby, the housing is decoupled from the drive member, enabling a free rotation of the drive member relative to the housing and the resetting of the piston rod to its start position.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Other features will become apparent from the following detailed description when considered in conjunction with the accompanying drawings.

BRIEF DESCRIPTION OF THE FIGURES

FIG. 1 is a perspective view of an embodiment of a drive member having a track,

FIG. 2 is a perspective view of an embodiment of a ramp ring,

FIG. 3 is a perspective view of an embodiment of a unidirectional element,

FIG. 5D is a perspective view of the dispense mechanism of the drug delivery device of FIG. 4A after a dose set operation, FIG. 5E is a perspective view of the biasing means of the drug delivery device of FIG. 4A before backing-off at the end of a dose dispense operation, FIG. 5F is a perspective view of the biasing means of the drug delivery device of FIG. 4A after backing-off at the end of a dose dispense operation, FIG. 6A is a perspective cut-away view of the drug delivery device of FIG. 4A after the last dose has been dispensed, FIG. 6B is an enlarged view of the blocking of the dispense mechanism of the drug delivery device of FIG. 4A after the last dose has been dispensed, FIG. 8B is a perspective cut-away view of the drug delivery device of FIG. 4A during a priming operation.

DETAILED DESCRIPTION

Figure 4A:
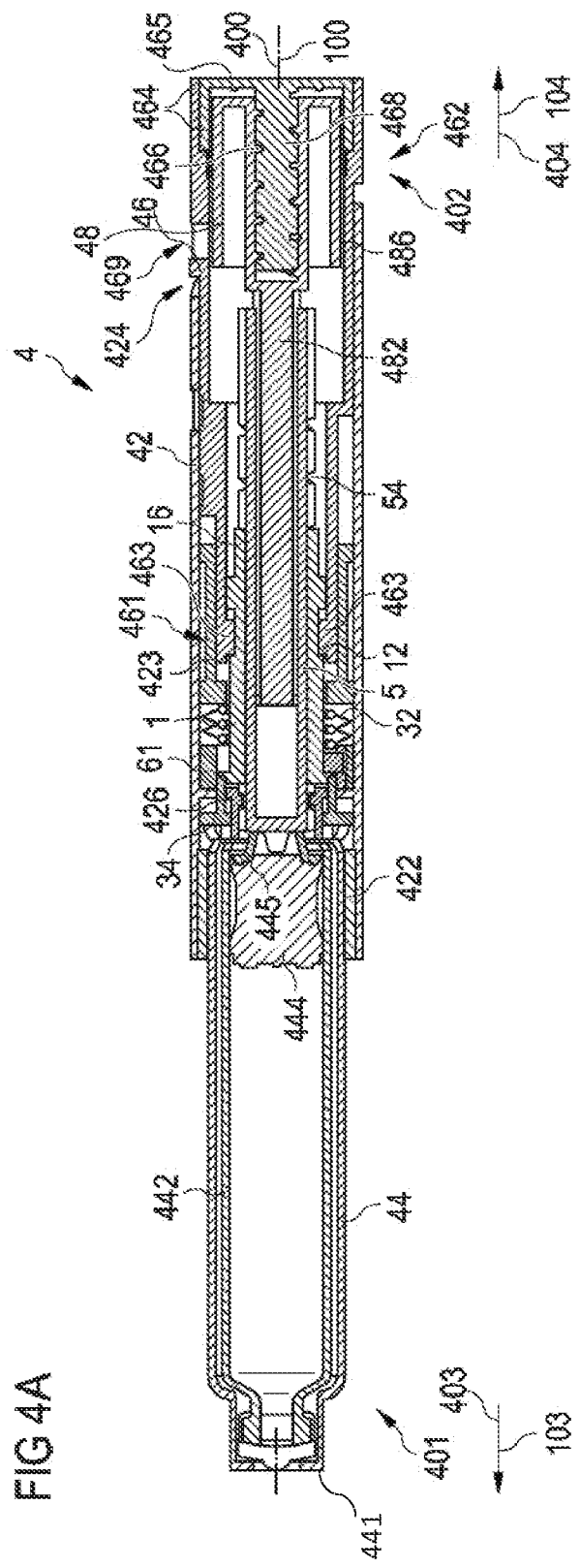
FIG. 4A is a perspective cross-sectional view of a first embodiment of a drug delivery device.

FIG. 1 shows a drive member 1 for driving a piston rod in a drug delivery device. The piston rod may act on a bung inside a cartridge containing a medicament. As an example, the medicament may be a liquid medicament such as GLP-1 or heparin. Preferably, the drive member 1 is directly engaged with the piston rod and drives the piston rod towards a distal direction of the cartridge, whereby the medicament is pressed out of the cartridge.

The depicted drive member 1 has the shape of a sleeve extending along a longitudinal axis 100. On its outer surface 105, the drive member 1 has a track 12 having a contact face 120 for transmitting a driving load from an actuating member to the drive member 1. Preferably, the drive member 1 is configured for being rotationally driven by an actuating member, wherein the actuating member is constrained to an axial movement along the longitudinal axis 100. As an example, an actuating member may be fixed to a dose member operable by a user for setting and dispensing a dose of a medicament. In particular, the actuating member may be an integral part of a dose member. In further embodiments, the actuating member may be coupled to a dose member such that the movement of the dose member is transferred to the actuating member.

The drive member 1 is particularly suitable for a fixed-dose drug delivery device. In such a device, the absolute size of a dose to be dispensed is predetermined by the design of the drive mechanism of the drug delivery device. In particular, a user does not have the option of varying the dose. In this context, setting a dose means that the drug delivery device is prepared for a subsequent dose dispense operation.

The drive member 1 may be suitable for a pull-push drug delivery device, wherein by pulling a dose member in a proximal direction of the drug delivery device a dose of medicament can be set and by pushing the dose member in a distal direction, the medicament can be dispensed. However, the drive member 1 may also be suitable for other mechanisms, for example a push-push device, wherein a dose member is pushed for setting a dose and pushed for dispensing a dose.

The depicted drive member 1 is configured for an engagement with a piston rod such that the piston rod is rotationally fixed to the drive member 1 and at least partially free to move along the longitudinal axis 100 of the drive member 1.

In the shown embodiment, the drive member 1 is configured to at least partly enclose a piston rod. For this aim, at its inner surface 106, the drive member 1 comprises one or more male splines 16 engagable with female splines of a piston rod. The male splines 16 extend along the length of the drive member 1.

In further embodiments, instead of male splines 16, a drive member may comprise female splines engaging with male splines of a piston rod. Alternatively, a drive member may comprise a flat section extending along the longitudinal axis 100 at its surface 106 and differing from the mainly circular inner cross section of the inner surface 106. A suitable piston rod has a matching flat section engageable with the flat section of the drive member, thereby locking the piston rod rotationally to the drive member and allowing a relative translational movement.

The drive member 1 is configured such that a movement of the drive member 1 can be actuated by an actuating member exerting a load on the contact face 120 of the track 12. The track 12 encircles the outer surface 105 of the drive member 1. When following the track 12 in one direction relative to the track 12 the direction of the movement along the track 12 changes from the proximal direction 104 into the distal direction 103. Here, the track 12 is constrained between a first axial position 107 and a second axial position 108, thereby oscillating between these positions 107, 108.

In different embodiments, for example when the drive member is designed for a drug delivery device where the sizes of subsequent doses differ, the track may run in a distal direction from a first axial position towards a second axial position and then towards the proximal direction but not reach the first axial position again.

The track 12 comprises dose set sections 122, each followed by a dose dispense section 125. The drive member 1 comprises a total of four dose dispense sections 125 and four dose set sections 122. In a different embodiment, a drive member may contain more or less than four dose set 122 and dispense sections 125. The track 12 is closed in itself such that the fourth dose dispense section 125 is directly followed by the first dose set section 122. Thereby, the drive member 1 is in principle not limited to a specific number of doses to be set and dispensed.

The drive member 1 is configured such that during setting a dose, an actuating member contacts a dose set section 122 and during dispensing a dose, the actuating member contacts a dose dispense section 125. Thereby, the contact area between an actuating member and the drive member follows the track 12 in one direction.

The track 12 is designed such that during dose setting and dispensing an axial load exerted by an actuating member is redirected into a rotational load onto the drive member 1.

For this aim, the contact face 120 of at least a part of the dose dispense section 125 is inclined relative to the longitudinal axis 100 of the drive member 1 in an angle larger than 0° and smaller than 90°. Thereby, when an actuating member contacting a part of the contact face 120 is pushed in the distal direction 103, the drive member is caused to rotate around the longitudinal axis 104 in a first rotational direction 110, while the contact area between the actuating member and the drive member 1 moves along the dose dispense section 125 in the distal direction 103.

The inclination angle of the contact face 120 relative to the longitudinal axis affects the mechanical advantage of a drug delivery device. In particular, a larger inclination angle will result in a lower mechanical advantage. The dose dispense section 125 comprises two inclined parts 125a, 125b, each with absolute values of inclination angles larger than 0° and smaller than 90°. The first part 125a has a smaller inclination angle than the second part 125b. This may help to achieve a force needed to push an actuating member towards the distal direction 103 which is substantially constant within one complete pushing action, even in the case when, at the end of the dose dispense operation, the drive member 1 interacts with further components of the drug delivery device thus increasing the effective torque needed to move the drive member.

For setting a dose, an actuating member contacting a part of the contact face 120 is pulled towards the proximal direction 104, wherein the contact area between the actuating member and the drive member 1 moves along the dose set section 122 in the proximal direction 104 towards the second axial position 108. The dose set section 122 comprises a part 122b being inclined to the longitudinal axis 100 of the drive member 1 with the absolute value of an inclination angle larger than 0° and smaller than 90°, wherein the contact face 120 points towards the distal direction 103. Here, an axial movement of the actuating member in the proximal direction 104 results in a movement towards a second rotational direction 111 opposite to the first rotational direction 110. Preferably, a suitable actuating member has a curved shape enabling contacting the contact face 120 both on the dose dispense section 125 and the dose set section 122.

Furthermore, the dose set section 122 comprises a first part 122a being parallel to the longitudinal axis 100. In further embodiments, a drive member may be free of such a first part 122a or may comprise additional parts of the track 12.

Preferably, when an actuating member has been fully pulled out in the proximal direction 104 the drive member 1 carries out a small rotational movement towards the first rotational direction 110. In this case, when subsequently pushing the actuating member towards the distal direction 103 the actuating member contacts the drive member 1 on the adjacent dose dispense section 125.

At its distal end 101, the drive member 1 comprises a bias track 14 having a contact surface 140 for transmitting a bias load on the drive member 1 towards a small rotation around the longitudinal axis 100. The bias track 14 is located at the distal part of a flange 13. The flange 13 may serve to define or constrain the axial position of the drive member 1 relative to a housing of a drug delivery device.

The bias track 14 comprises a first redirecting section 142 and a second redirecting section 143, wherein both sections 142, 143 are inclined with the absolute value of the inclination angles larger than 0° and smaller than 90° towards the longitudinal axis 100 of the drive member 1. Both redirecting sections 142, 143 redirect an axial load into a rotational load around the longitudinal axis 100.

The first redirecting section 142 is configured such that, through an interaction with further component of biasing means, at the end of a dose set operation, a bias is exerted towards the first rotational direction 110. Thereby, a small rotation of the drive member 1 in the first rotational direction 110 may be caused when the actuating member is fully pulled in the proximal direction 104 and is out of contact with the track 12 on the drive member 1.

The second redirecting section 143 is configured such that at the end of a dose dispense section 125 a bias is exerted into the second rotational direction 111. This bias may lead to a small back-rotation towards the second rotational direction 111 of the drive member 1, when the actuating member is released. Thereby, a backing-off of the dispense mechanism and in particular of the piston rod may be achieved.

Thus, a bung inside a cartridge is free to relax towards the proximal direction 104 of the drug delivery device, whereby a dripping of medicament out of the cartridge after dose dispense can be reduced.

The first and second redirecting sections 142, 143 are arranged adjacent to each other, thereby forming a recess 144 in the bias track 14. Several such recesses 144 are provided along the bias track 14, being spaced by neutral sections 145 running perpendicular to the longitudinal axis 100. In a further embodiment of the bias track 14, the recesses 144 are directly adjacent to each other.

Furthermore, at its outer surface 105, the drive member 1 comprises lugs 17 configured for a mechanical interaction with an element providing feedback to a user at defined operation states of the drug delivery device, for example after a dose dispense or dose set operation. Such an element may have the shape of a feedback element as shown in FIG. 3.

FIG. 2 shows a ramp ring 34 configured to contact a drive member 1 at the bias track 14 as shown in FIG. 1. The ramp ring 34 is a component of biasing means exerting a bias on the drive member 1 towards a first 110 and second rotational direction 111 at specific phases of operation of a drug delivery device.

The ramp ring 34 has the shape of a ring having a central axis configured to be aligned with the longitudinal axis 100 of the drive member 1 in an assembled state of a drug delivery device. At its proximal end 341, the ramp ring 34 comprises bias lugs 343 configured for transmitting a load onto the contact surface 140 of the bias track 14 of the drive member 1. When the drive member 1 rotates around the longitudinal axis 100, the contact area between the bias lugs 343 and the drive member 1 runs along the contact surface 140 of the bias track 14. The bias lugs 343 comprise a first inclined face 345 configured for contacting a first redirecting section 142 of the bias track 14 of the drive member 1 and a second inclined face 346 configured for contacting a second redirecting section 143 at certain operation states of a drug delivery device. Between the first 345 and second redirecting sections 346, the bias lug 343 comprises a peak 344 configured to contact the bias track 14 at its neutral sections 145 and at the center 141 of the recess 144.

The ramp ring 34 comprises coupling means 348 configured for coupling the ramp ring 34 to a housing of a drug delivery device such that a limited axial movement relative to the housing is allowed and a rotational movement is prevented. In further embodiments, the coupling means 348 may be configured such that both an axial and rotational movement of the ramp ring 34 relative to a housing is prevented. Preferably, in the case that a relative axial movement is prevented, the drive member is configured such that a limited axial movement between a housing and the drive member is allowed.

Furthermore, at its distal end 342, the ramp ring 34 comprises engagement means 347 configured for engagement with a part of a cartridge holder housing a cartridge. The engagement means 347 are configured such that during assembly, the cartridge holder pushes the ramp ring 34 into contact with the drive member 1. Preferably, a drug delivery device comprises a spring exerting an axial bias on one of the drive member 1 and the ramp ring 34 towards the other one of the drive member 1 and the ramp ring 34. Preferably, here, the spring is tensioned by pushing a cartridge holder in the proximal direction 104 of the drug delivery device.

When the bias lugs 343 contact the first 142 or second redirecting section 143 of the bias track 14 on the ramp ring 34, the load towards the axial direction is redirected into a load into a rotational direction. In particular, when the bias lug 343 contacts the track 12 on the drive member 1 at the first redirecting section 142 a bias of the drive member 1 towards the first rotational direction 110 is created. When the bias lug 343 contacts the track 12 on the drive member 1 at the second redirecting section 143 a bias towards the second rotational direction 111 is created. At the center 141 of the recess 144 and at neutral sections 145 the drive member 1 is unbiased towards the rotational directions.

Furthermore, at its proximal end 341, the ramp ring 34 comprises feedback lugs 349 configured for contacting means for providing feedback to a user at defined operation phases of the drug delivery device, for example after a dose dispense or dose set operation. Such means may have the shape of a feedback element as shown in FIG. 3.

FIG. 3 shows a feedback element 61 for providing audible and tactile feedback to a user at the end of a dose dispense operation. The feedback element 61 has the shape of a ring, configured such that in an assembled state of a drug delivery device, its central axis aligns with the longitudinal axis 100 of the drive member 1.

At its inner surface, the feedback element 61 comprises slots 62 configured for accommodating the lugs 17 at the outer surface 105 of the drive member 1. Thereby, the feedback element 61 is coupled to the drive member 1 such that only a limited relative rotational movement is allowed.

Furthermore, at its distal end 66, the feedback element 61 comprises a ramped contact face 64, configured for a mechanical interaction with the feedback lugs 349 at the ramp ring 34. The ramped contact face 64 is shaped such that in a first rotational direction 110 of the feedback element 61 relative to the ramp ring 34, the relative movement of the feedback element 61 and the ramp ring 34 is unrestricted. In particular, a relative movement of the feedback lugs 349 over ramps 65 of the ramped contact face 64 is allowed, whereby tactile and audible feedback is created. In a second rotational direction 111 opposite to the first rotational direction 110, the relative movement of the feedback element 61 and the ramp ring 34 is restricted. Here, the ramps 65 prevent a relative back-rotation of the feedback element 61. Thus, the feedback element 61 can be a unidirectional element 6 preventing the free rotational movement of the drive member 1 relative to a housing of a drug delivery device in a certain rotational direction.

Figure 4B:
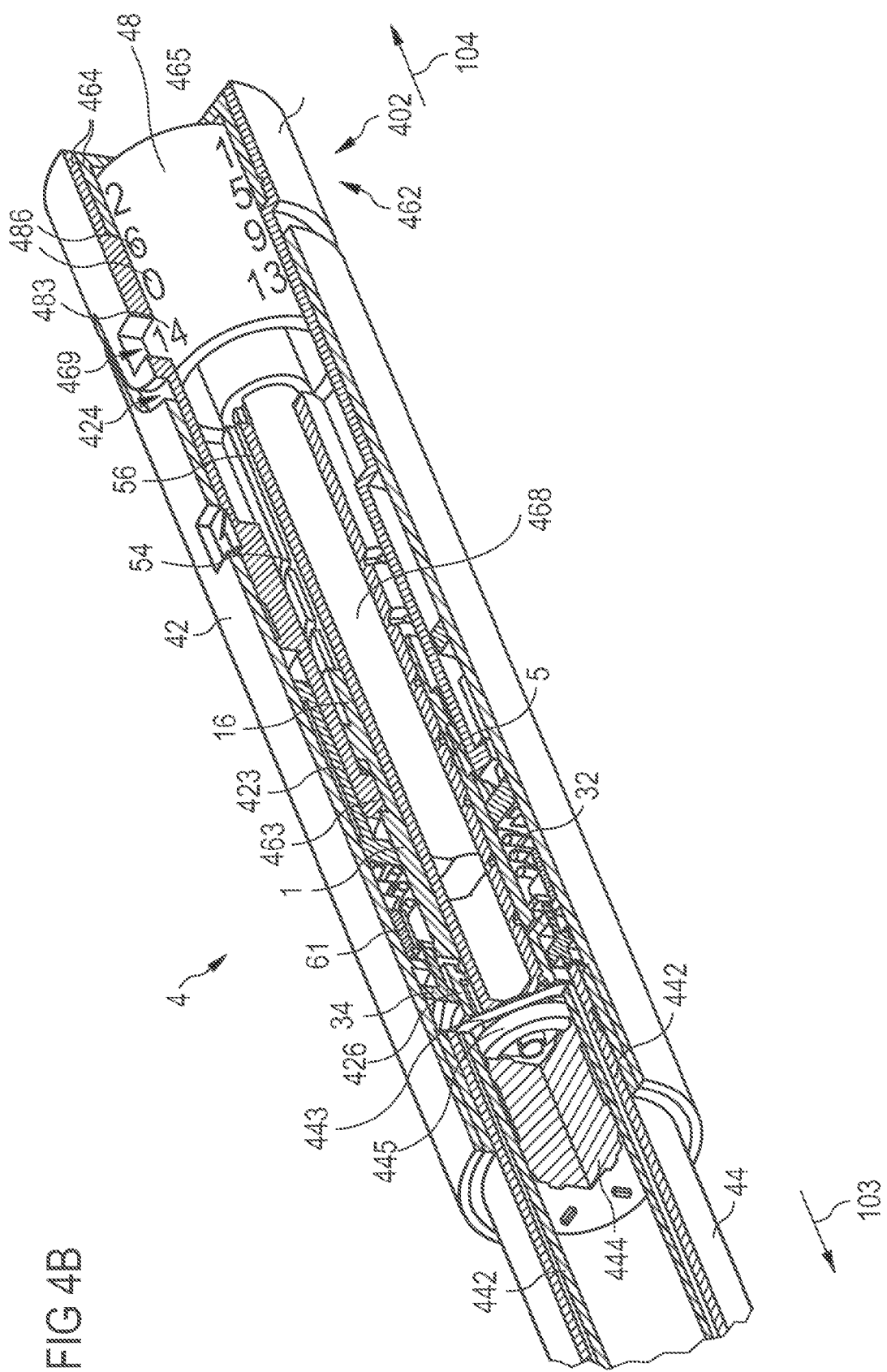
FIG. 4B is a cut-away view of the first embodiment of a drug delivery device of FIG. 4A.

FIGS. 4A and 4B show a first embodiment of a drug delivery device 4 for dispensing and setting doses of a drug. The drug delivery device 4 is a fixed-dose device, i.e., a user cannot choose the size of a dose to be dispensed. The drug delivery device 4 is a multi-dose device with a replaceable cartridge 442, wherein several subsequent doses can be dispensed from the cartridge 442 and wherein an empty cartridge 442 can be replaced.

The drug delivery device 4 comprises a main housing 42 to which a cartridge holder 44 comprising a cartridge 442 containing a liquid medicament is attached. As examples, the medicament may comprise GLP-1 or heparin. The cartridge holder 44 is screwed onto a threaded sleeve 422 fixed to the main housing 42 of the drug delivery device 4. In the assembled state, the cartridge 442 is pressed towards the distal end 441 of the cartridge holder 44 by a cartridge bias spring 443. When the cartridge holder 44 is removed from the main housing 42, the cartridge bias spring 443 is released and the empty cartridge 442 can be removed from the cartridge holder 44. After that, a new cartridge 442 can be inserted and the cartridge holder 44 can be reattached to the main housing 42.

In different embodiments, the cartridge holder 44 may be configured to be disposed with the empty cartridge 442, such that for replacing a cartridge, a new cartridge holder 44 is attached to the main housing 42.

The cartridge 442 contains a bung 444 which is moved in the distal direction 103 for dispensing the medicament through a needle unit (not shown here) at the distal end 401 of the drug delivery device 4. In particular, the bung 444 is in contact with a bearing 445 which moves with a piston rod 5 in the distal direction 103. The piston rod 5 is driven by a drive member 1 as shown in FIG. 1. The longitudinal axis 100, the distal direction 103 and the proximal direction 104 of the drive member 1 aligns with the longitudinal axis 400, the distal direction 403 and the proximal direction 404 of the housing 42.

At its proximal end 402, the drug delivery device 4 comprises a dose member 46 for setting and dispensing a dose of the medicament. The dose member 46 is coupled to a body chassis 423 which is fixed to the housing 42, such that a relative rotational movement of the dose member 46 and the housing 42 is prevented and a relative axial movement is allowed. Moreover, at its proximal end 462, the dose member 46 comprises a dose button 464 which protrudes through an opening 424 of the housing 42, also preventing a relative rotational movement between the housing 42 and the dose member 46.

For setting a dose of the medicament, the dose button 464 is pulled out of the main housing 42. Thereby, the drive mechanism is prepared for a subsequent dose dispense. On pushing the button 464 towards the distal direction 103, a dose can be dispensed. In different embodiments, the device may be configured such that both for setting and dispensing a dose a pushing movement of the dose button 464 is required.

The dose member 46 serves as an actuating member for exerting a load onto the drive member 1, causing a rotational movement of the drive member 1. For this aim, at its distal end 461, the dose member 46 comprises curved lugs 463 acting on the contact face 120 of the track 12 on the drive member 1.

The drive member 1 is coupled to the piston rod 5 such that a relative translational movement of the drive member 1 and the piston rod 5 is allowed and a relative rotational movement is prevented. For this aim, the drive member 1 comprises male splines 16 being guided in axial grooves 56 of the piston rod 5. In order to convert a rotational movement of the piston rod 5 into a combined rotational and axial movement of the piston rod 5, the piston rod 5 is threadedly engaged with a threaded sleeve 426 fixed to the housing 42. For this aim, the piston rod 5 comprises an outer thread 54.

The drug delivery device 4 comprises biasing means for, at the end of a dose set operation, exerting a bias on the drive member 1 towards a first rotational direction 110 and, at the end of a dose dispense operation, exerting a bias on the drive member 1 towards a second rotational direction 111. In particular, the biasing means comprise a spring 32 and a ramp ring 34 as shown in FIG. 2, interacting with the bias track 14 on the drive member 1. The ramp ring 34 is pressed onto the bias track 14 by the spring 32, whereby a load is exerted on the drive member 1.

The drug delivery device 4 further comprises a dose counter 48 which carries markings 486 on its outer surface indicating the number of remaining doses in the cartridge 442. The marking 483 representing the current filling state of the cartridge 442 is visible through an opening 469 in the dose button 464. The dose counter 48 is threadedly engaged with a rod-like part 468 of a button insert 465 fixed to the rest of the dose member 46. Thereby, a rotational movement of the piston rod 5 causes a combined translational and rotational movement of the dose counter 48.

Figure 5A:
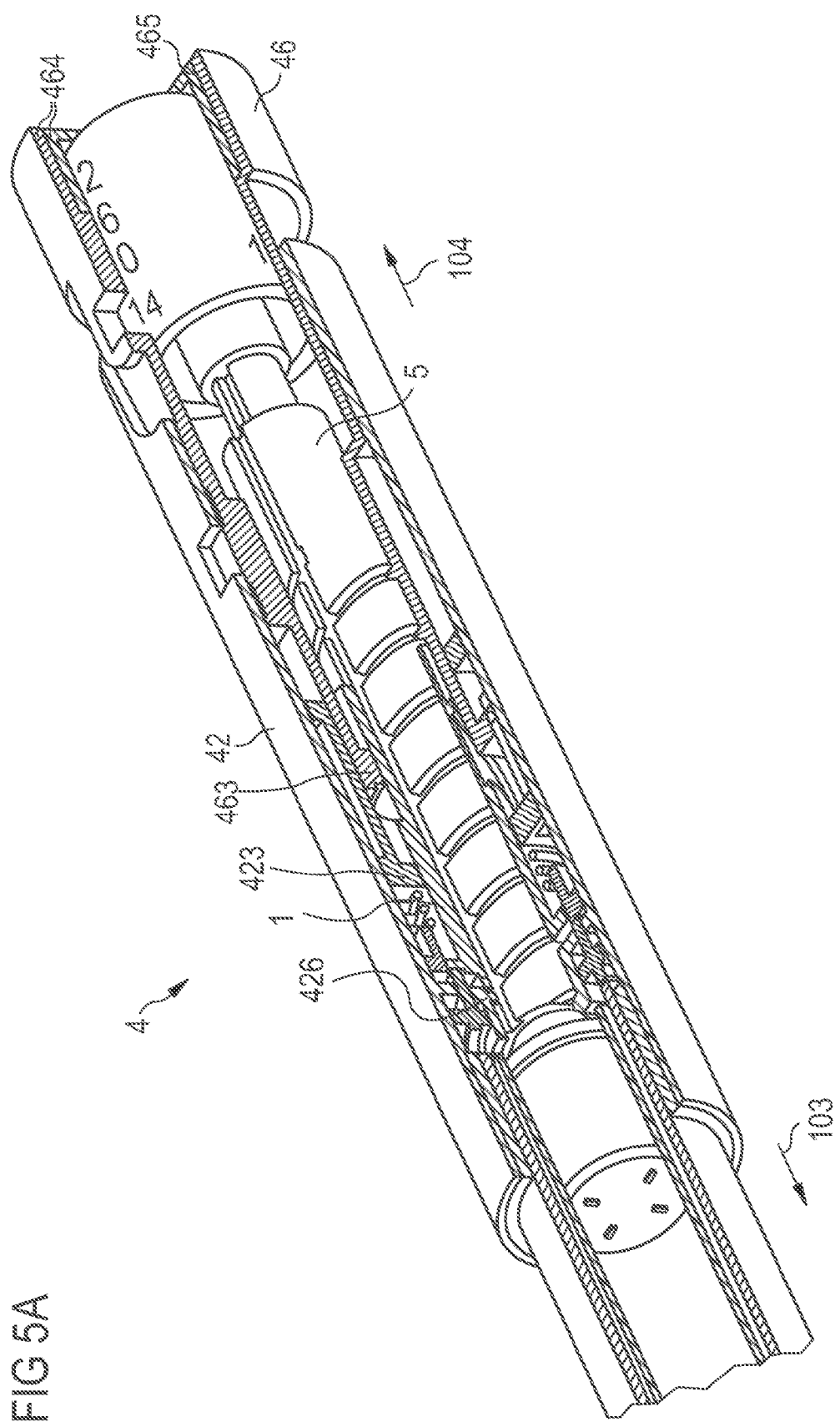
FIG. 5A is a perspective cut-away view of the drug delivery device of FIG. 4A during a dose set operation.
Figure 5B:
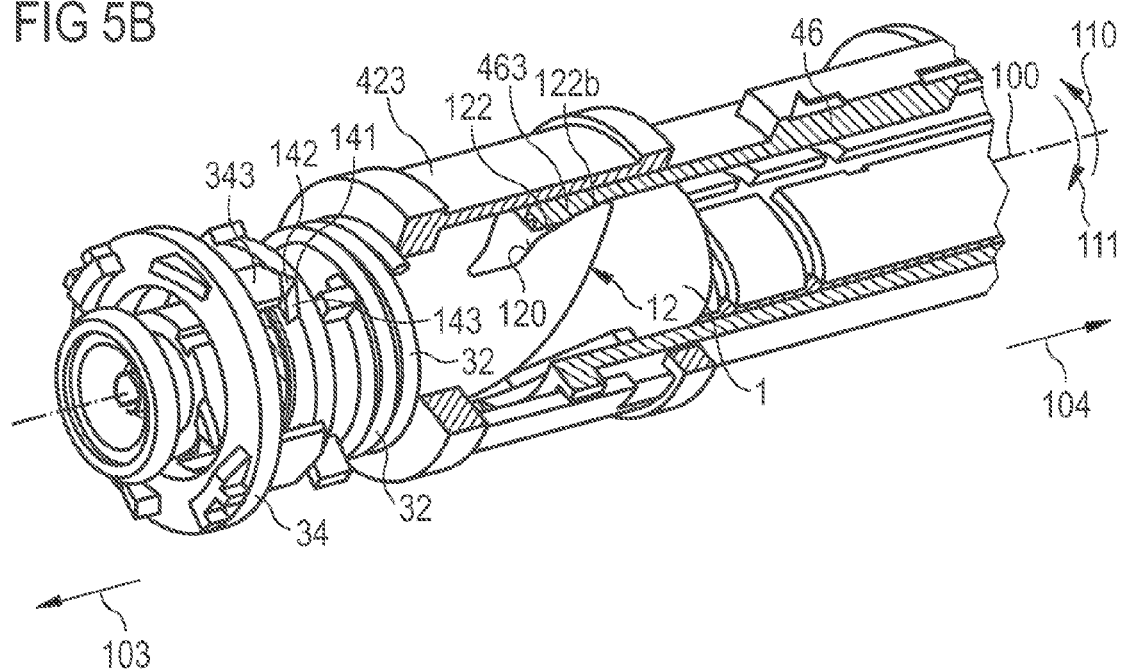
FIG. 5B is a perspective view of the dispense mechanism of the drug delivery device of FIG. 4A during a dose set operation.

FIG. 5A show the drug delivery device 4 of FIG. 4A and FIG. 5B shows its dispense mechanism during a dose set operation.

Here, FIG. 5A shows the drug delivery device 4, wherein the dose member 46 is pulled out in the proximal direction 104 by a user. Thereby, as can be seen in FIG. 5B, the lugs 463 at the distal end of the dose member 46 act upon the dose set section 122 of the track 12 on the drive member 1. When acting upon the inclined second part 122b of the dose set section 122, the lugs 463 exert a load onto the drive member 1 directed into the second rotational direction 111, causing a small rotation of the drive member 1 relative to the housing 42. Upon this rotational movement, the bias lugs 343 of the ramp ring 34 are driven up from the center 141 of the recess 144 on the first redirecting section 142 of the bias track 14. Due to its splined engagement with the drive member 1 and its threaded engagement with the threaded sleeve 426, here, the piston rod 5 carries out a small rotation and a small axial movement in the proximal direction 104.

At the end of the dose set operation, the lugs 463 of the dose member 46 clear the dose set section 122, thus allowing a small rotational movement of the drive member 1.

In particular, a bias spring 32 compressed by the chassis 423 and the lugs 17 on the drive member 1 presses the drive member 1 axially onto the bias lugs 343 of the ramp ring 34. This axial load is redirected into a rotational load by the interaction of the bias lugs 343 with the inclined first redirecting section 142. Thus, after the dose set operation, the drive member 1 carries out a small rotational movement relative to the housing 42. Thereby, the piston rod 5 carries out a small rotation and a small axial movement in the distal direction. The amount of movement of the piston rod 5 in the distal direction at the end of the dose set operation compensates the amount of movement of the piston rod 5 in the proximal direction during the dose set operation such that, in sum, the axial position of the piston rod 5 remains constant in a completed dose set operation. The movement of the drive member 1 at the end of the set operation may produce a feedback, for example a click, to a user, indicating that the device 4 has been set.

Figure 5C:
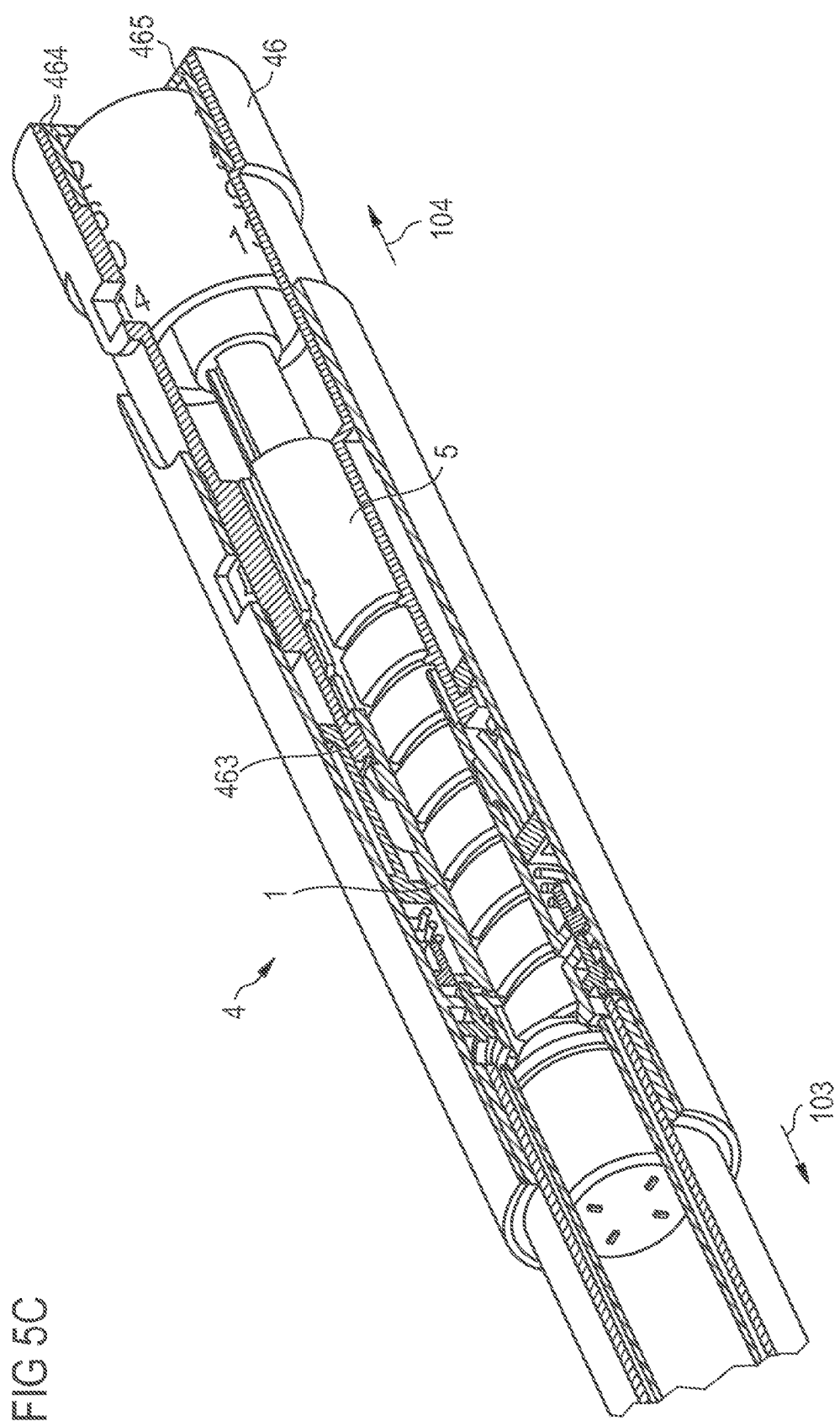
FIG. 5C is a perspective cut-away view of the drug delivery device of FIG. 4A after the dose set operation.

FIG. 5C shows the drug delivery device 4 of FIG. 4A and FIG. 5D shows its dispense mechanism after a dose set operation.

In particular, FIGS. 5C and 5D show the drug delivery device 4 after a dose set operation, when the drive member 1 has carried out a small rotational movement in the first rotational direction 110. The lugs 461 are now located at the dose dispense section 125 such that the drug delivery device 4 is ready for a subsequent dose dispense operation.

As can be seen in FIG. 5D, the contact area of the bias lugs 343 and the bias track 14 has moved from its unstable position at the first redirecting section 142 towards a stable position at the center 141 of the recess 144. Here, a further movement of the drive member 1 is prevented by the interaction of the bias lugs 343 with the second redirecting section 143 creating a bias in the opposite rotational direction.

At this stage, for dispensing a dose, the dose button 464 can be pushed towards the housing 42 of the drug delivery device 4. Thereby, the contact area between the lug 463 of the dose member 46 and the track 12 moves along the dose dispense section 125 in the distal direction 103. On dispensing the dose, the drive member 1 is driven towards the first rotational direction 110. Thereby, also the piston rod 5 is driven towards a movement in the first rotational direction 110 and simultaneously carries out an axial movement in the distal direction 103.

FIG. 5E shows the biasing means 3 of the drug delivery device of FIG. 4A at the end of a dose dispense operation.

During the dose dispense operation, caused by the rotational movement of the drive member 1, the contact area between the bias lugs 434 moves up the second redirecting section 143 of the bias track 14. Thereby, a bias on the drive member 1 into the second rotational direction 111 is created. At the end of the dose dispense operation, when the dose member 46 is released, the drive member 1 is free to carry out a small rotational movement in the second rotational direction 111. Thereby, also the piston rod 5 is driven towards the second rotational direction 111 and simultaneously carries out a small axial movement into the proximal direction 104. This allows a backing-off of the bung 444 in the proximal direction 104, whereby the dripping of a drug out of the drug delivery device 4 after dose dispense can be prevented.

FIG. 5F is a perspective view of the biasing means 3 of the drug delivery device 4 of FIG. 4A after backing-off at the end of a dose dispense operation.

Here, it can be seen that the bias lugs 343 have moved towards the centre 141 of the recess 144 of the bias track 14 for causing a backing-off action. Thus, the bias lugs 343 have reached a stable rotational position at the bias track 14 of the drive member 1. Accordingly, the drive member 1 has reached a stable state, being unbiased in any rotational direction.

FIG. 6A shows the drug delivery device 4 according to FIGS. 4A and 4B after the last available dose has been dispensed from the cartridge 442. Here, the dose button 464 has been fully pushed out in the proximal direction 104 of the drug delivery device 4 for setting a subsequent dose. Thus, the drug delivery device 4 is configured such that a dose set operation is enabled after the last dose has been dispensed. However, in this state, pushing the dose member 464 in the distal direction 103 is prevented by a mechanical interaction of the threaded sleeve 426 and the end of the outer thread 54 of the piston rod 5. In particular, after the last dose has been dispensed, the threaded sleeve 426 reaches the end of the outer thread 54 and, on a further movement of the piston rod 5, abuts a stop face 55. Here, the blocking strength of the mechanism can be enforced by adding a radial protrusion at the end of the outer thread 55 of the piston rod 5. Thereby, a bump-over of the threaded sleeve 426 over the end of the outer thread 54 can be prevented.

By the mechanical interaction of the threaded sleeve 426 and the stop face 55, a further rotation of the piston rod 5 and the drive member 1 relative to the housing 42 is blocked. Therewith, also the dose button 464 is blocked from being pushed towards the housing 42. Thus, the dose button 464 remains in its pulled-out position.

Figure 7A:
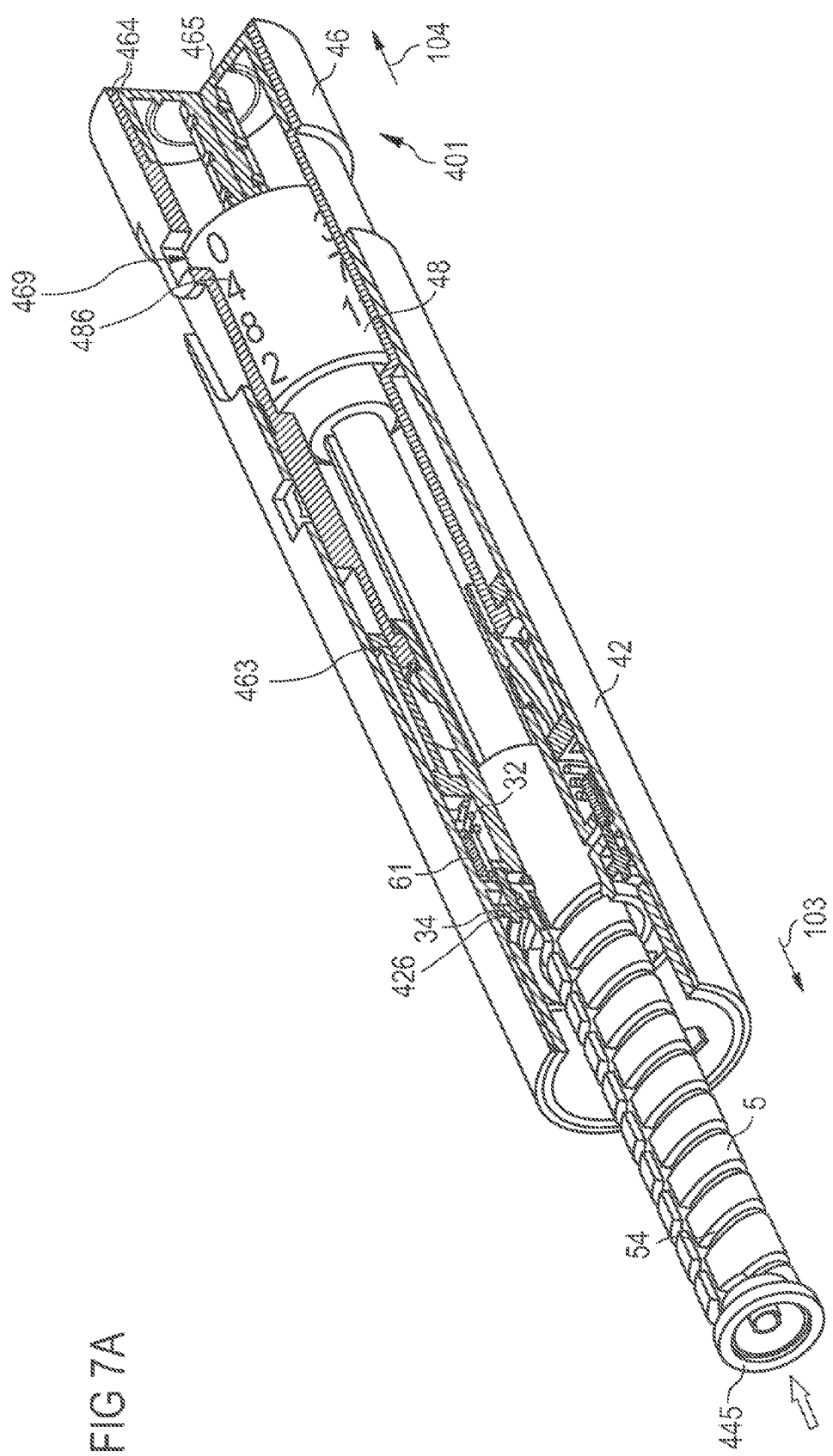
FIG. 7A is a perspective cut-away view of the drug delivery device of FIG. 4A during resetting.
Figure 7B:
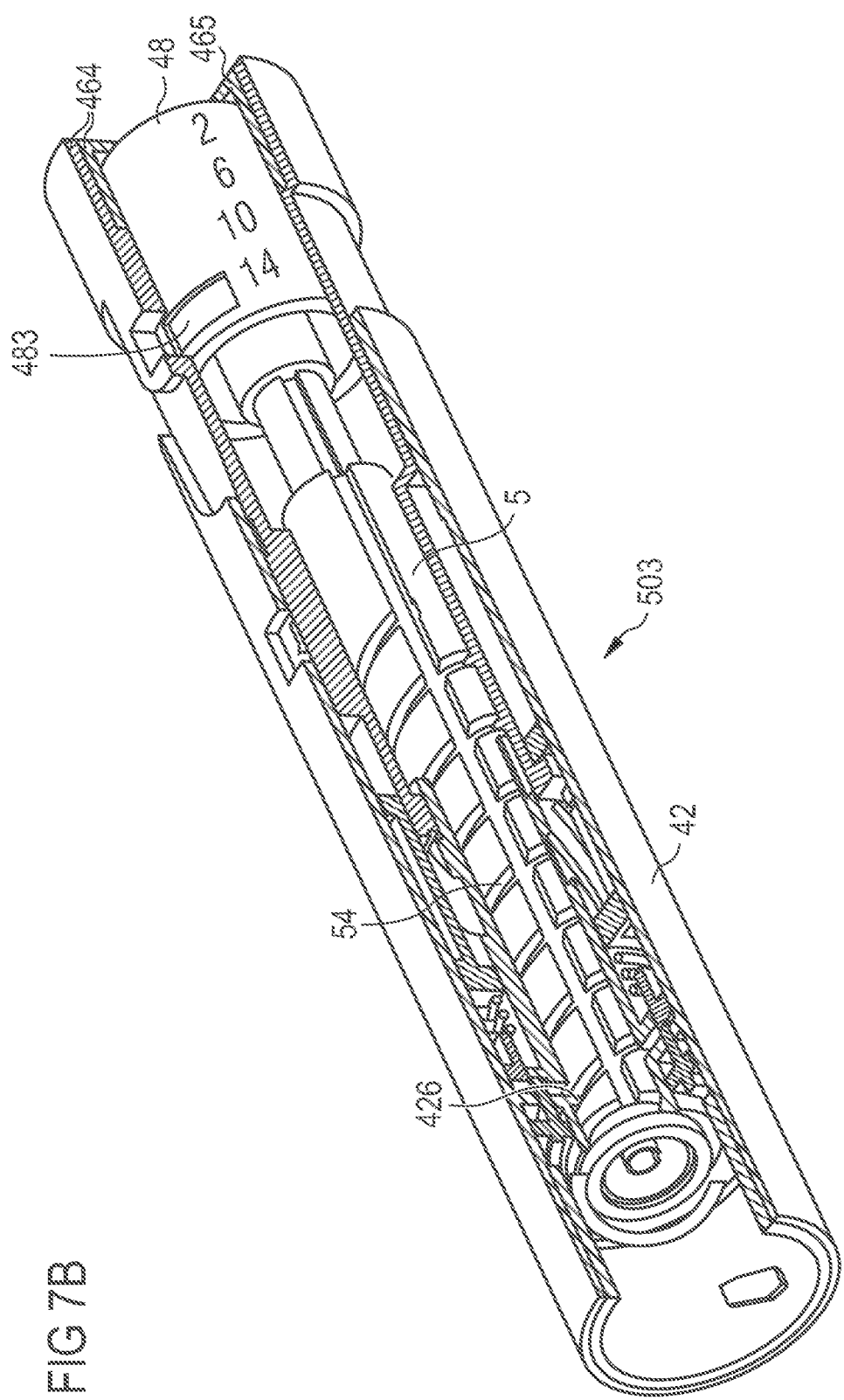
FIG. 7B is a perspective cut-away view of the drug delivery device of FIG. 4A after resetting.

FIGS. 7A and 7B show a resetting of the drug delivery device 4 of FIG. 4A. Here, FIG. 7A shows the device 4 before a resetting operation and FIG. 7B the device 4 after the resetting operation.

In this context, "resetting" means that the piston rod 5 is moved backwards in the proximal direction 104 to a start position relative to the housing 42 after several or all doses of a medicament have been dispensed. Thereby, after an empty cartridge 442 is removed, the dispense mechanism is reset to a start state and a new cartridge can be mounted to the drug delivery device 4.

In order to remove the used cartridge 442, the cartridge holder 44 is detached from the main housing 42 of the drug delivery device 4. Thereby, elements preventing or hampering the backwards movement of the piston rod 5 in the proximal direction 104 are disengaged. In particular, the spring 32 is enabled to relax, whereby the feedback element 61 is disengaged from the drive member 1. Furthermore, the ramp ring 34 is disengaged from the drive member 1 and from the feedback element 61 such that a free rotation of the drive member 1 is enabled.

Then, by applying a force on the bearing 445 and thereby on the piston rod 5 in the proximal direction 104, the piston rod 5 will overhaul and rotate through its threaded engagement with the threaded sleeve 426. Therewith, also the drive member 1, the feedback element 61 and the dose counter 48 will rotate backwards to their respective start positions. When the dose counter 48 has been fully rotated backwards, which can be seen in FIG. 7B, the marking 483 visible through the opening 469 indicates that the drug delivery device 4 has been reset.

In this embodiment, resetting the dispense mechanism requires that the dose member 46 is in a pulled-out position such that the lugs 463 do not hinder a free backward rotation of the drive member 1. In the case that the user has pulled the dose button 464 out of the housing 42 after the last available dose has been dispensed, the dose member 46 is already in a position allowing a resetting of the mechanism. If the dose button 464 has not been pulled out of the housing 42 or has not been fully pulled out of the housing 42, the dose member 46 may be pushed out towards the proximal direction 104 by the backwards rotation of the drive member 1. Here, depending on the thread pitches, the dose member may not overhaul on its own and, thus, may require user input.

Once the piston rod 5 has been fully pushed back into its start position 503, the cartridge holder 44 containing a new medicament cartridge 442 can be reattached to the drug delivery device 4. Thereby, the ramp ring 34 is reengaged with the drive member 1 and the feedback element 61, automatically aligning the components in their correct positions. The cartridge bias spring 443 is tensioned, thereby pressing the cartridge 442 towards the distal end 441 of the cartridge holder 44.

Here, instead of directly manually pushing the piston rod 5 towards its start position 503, it may be pushed by the cartridge 442 and the cartridge holder 44. Furthermore, the drug delivery device 4 may be configured such that after the cartridge holder 44 has been removed, the piston rod 5 returns to its start position 503 by itself on orienting the drug delivery device 4 with its distal direction 103 showing upwards. Such a resetting of the piston rod 5 by its own weight may be enabled by a sufficiently low friction between the elements of the drive mechanism.

Figure 8A:
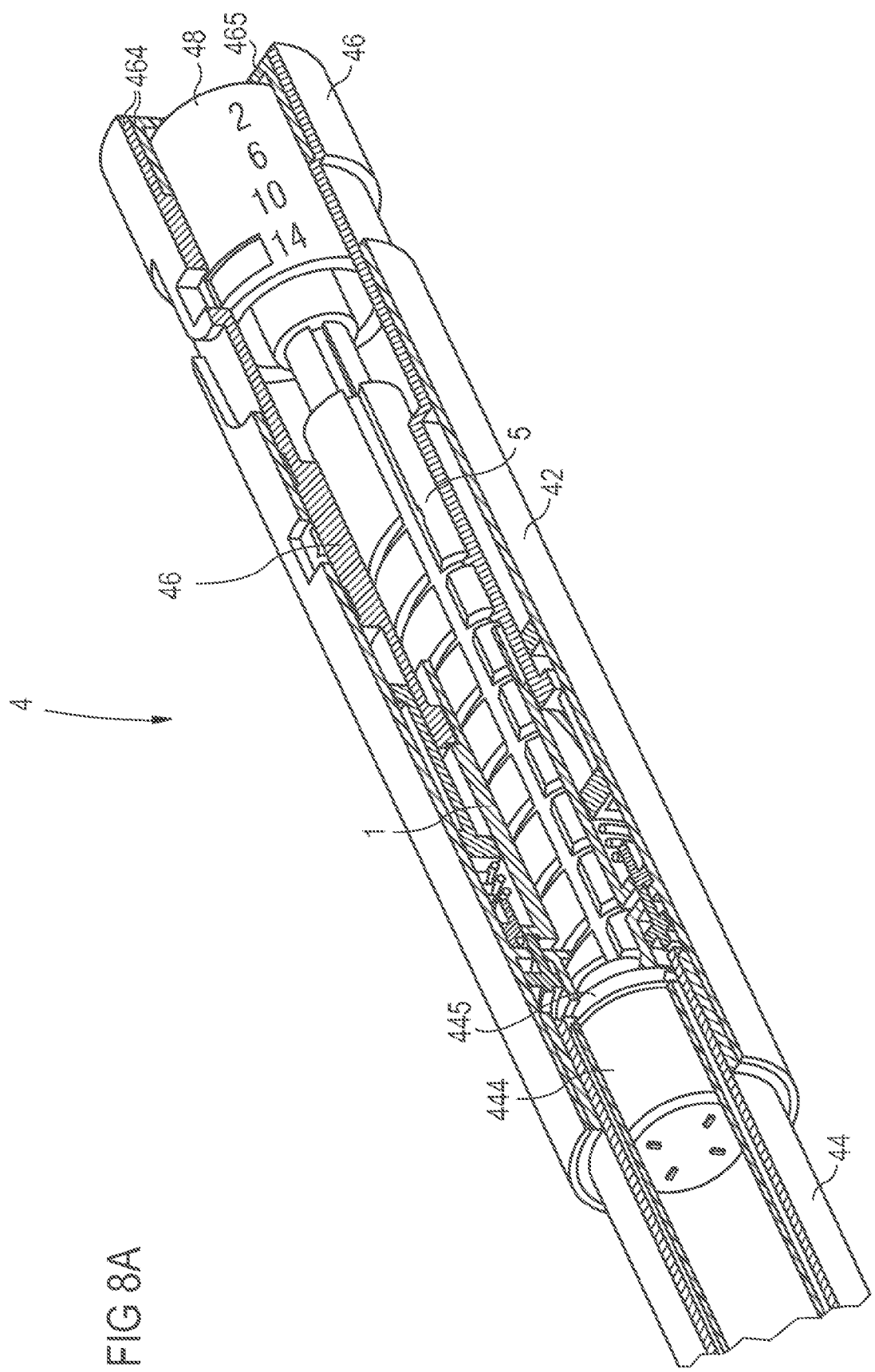
FIG. 8A is a perspective cut-away view of the drug delivery device of FIG. 4A after a new cartridge has been inserted.

FIG. 8A shows the drug delivery device 4 of FIG. 4A after the resetting operation, when the cartridge holder 44 has been reattached to the housing 42. Here, the piston rod 5, the drive member 1, and the dose counter 48 are at their respective start positions.

The dose member 46 and thereby also the dose button 464 are in their pulled-out positions, indicating that the drug delivery device 4 is ready for a priming operation. Here, "priming" means that after resetting the device and after a new cartridge has been inserted, the dispense mechanism is actuated such that the gaps between the different parts of the dispense mechanism are removed. Here, for example, after pushing the piston rod 5 in the proximal direction 104 for resetting the device, gaps may have been created between the bung 444 and the bearing 445, between the bearing 445 and the piston 5, between the piston 5 and the drive member 1 and between the dose member 46 and the drive member 1. By removing these gaps, an accurate setting and dispensing of the first dose is enabled after the drug delivery device 4 has been primed.

FIG. 8B shows the drug delivery device 4 of FIG. 4A directly after a priming operation.

Here, the dose member 46 has been pushed towards the housing 42, whereby the dispense mechanism has carried out a dose dispense movement, as has been described above. Here, depending on the existing gaps, a small amount of medicament will be pressed out of the cartridge 442.

Figure 8C:
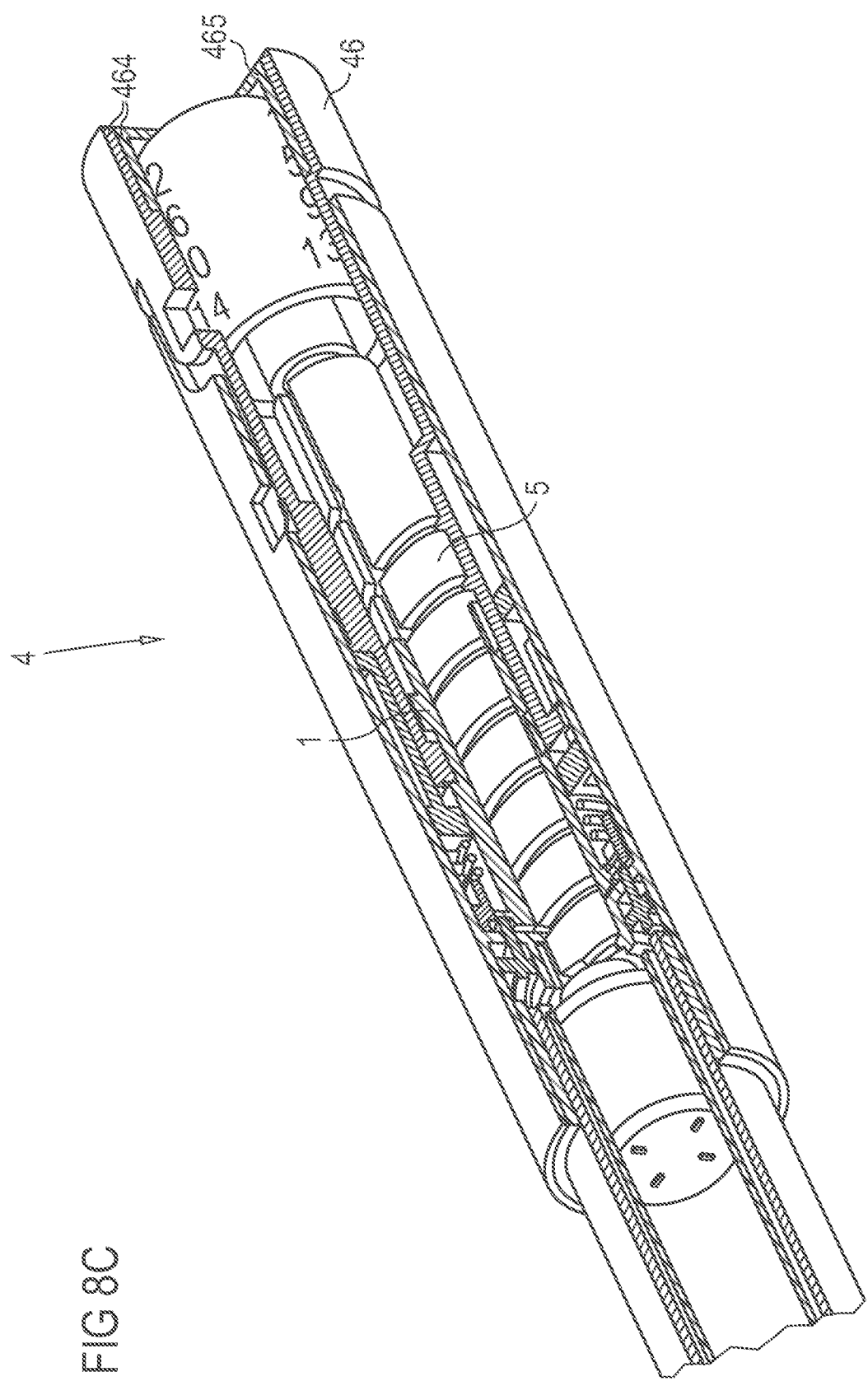
FIG. 8C is a perspective cut-away view of the dispense mechanism after backing-off after a priming operation.

FIG. 8C shows the drug delivery device 4 after the priming operation, when the dispense mechanism has carried out a backing-off movement. Here, the drive member 1 has carried out a small backwards rotational movement, causing the dose member 46 to carry out a small movement in the proximal direction 104. This backing-off operation corresponds to the backing-off during a dose dispense operation as has been already described above.

Figure 9A:
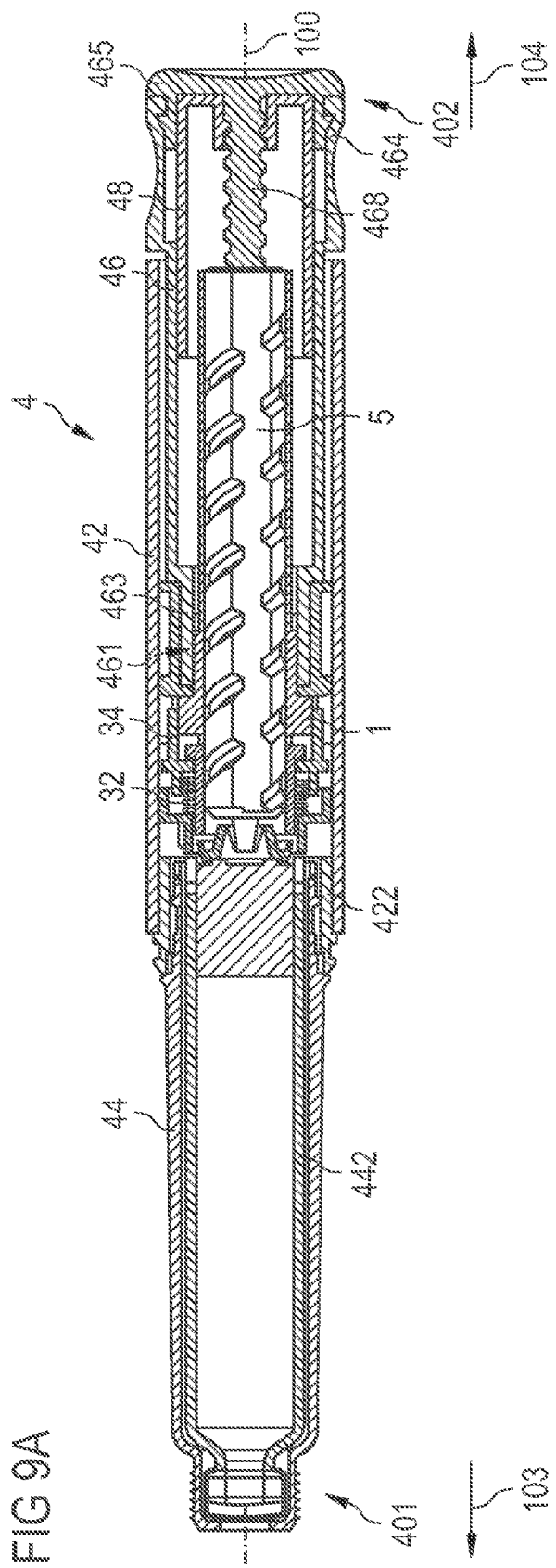
FIG. 9A is a perspective cross-sectional view of a second embodiment of a drug delivery device.
Figure 9B:
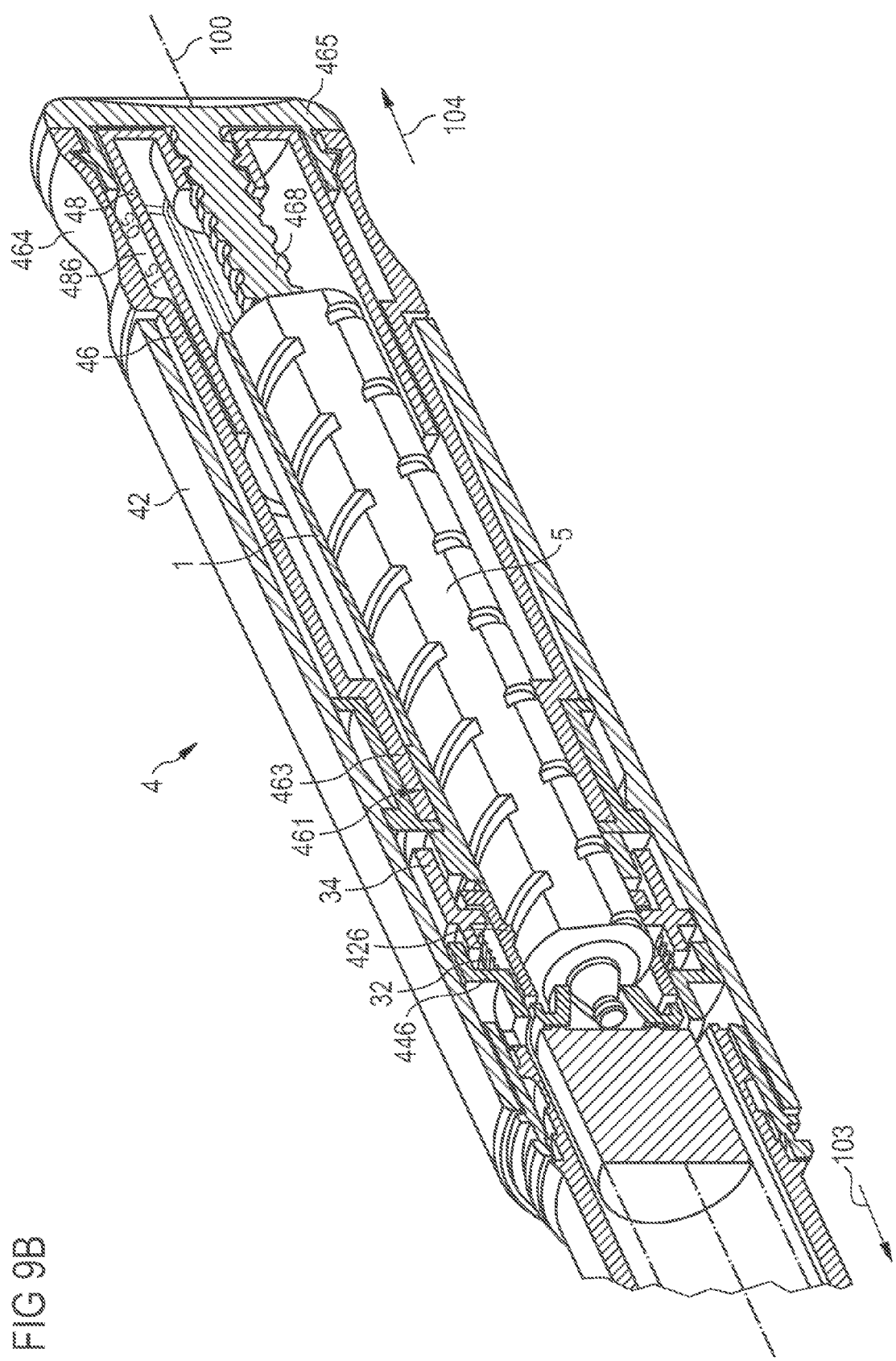
FIG. 9B is a perspective cut-away view of the second embodiment of the drug delivery device of FIG. 9A.

FIGS. 9A and 9B show a second embodiment of a drug delivery device 4, wherein the number of parts has been reduced compared to the drug delivery device according to FIGS. 4A and 4B.

The drug delivery device 4 comprises a main housing 42 to which a cartridge holder 44 comprising a cartridge 442 is attached. The cartridge holder 44 is screwed onto a threaded sleeve 422 fixed to the main housing 42. At its proximal end 402, the drug delivery device 4 comprises a dose button 465 which is part of a dose member 46 for setting and dispensing a dose of a medicament. At its distal end 461, the dose member 46 comprises a lug 463 for activating the drive member 1 and thereby causing a rotational movement of the drive member 1 around the longitudinal axis 100 of the device 4.

The drug delivery device 4 comprises a ramp ring 34 pressed towards the drive member 1 by a bias spring 32. The bias spring 32 is located between the ramp ring 34 and a bias ring 446 and also exerts an axial load on the cartridge 442 towards the distal end 441 of the cartridge holder 44. Thus, in this embodiment, the bias spring 32 serves for exerting an axial load both on the cartridge holder 442 and on the ramp ring 34. In this embodiment, the biasing is due to the ramp ring 34 moving axially up and down biasing faces on the drive member 1. Accordingly, here, the ramp ring 34 reciprocates axially, while the drive member 1 is constrained to a rotational movement. In contrast to that, in the embodiment shown in FIG. 4A, the drive member 1 reciprocates axially and carries out a rotational movement while the ramp ring 34 is fixed to the housing 42.

The depicted drug delivery device 4 does not comprise an additional feedback element. Here, a feedback function is integrated into the ramp ring 34. Furthermore, the ramp ring 34 and the bias spring 32 have been removed from the load path of the drive member 1, whereby the friction of the dispense mechanism is reduced.

Also in this embodiment, the drug delivery device 4 comprises a dose counter 48 for displaying the number of remaining doses to a user. The dose counter 48 is in threaded engagement with a rod-like part 468 of a button insert 465 of the dose member 46. Here, the dose counter 48 is driven by the drive member 1. It partially encloses the drive member 1 and is in splined engagement with the drive member 1. For this aim, at its inner surface, the dose counter 48 comprises an axial flat section being engaged with a matching flat section of the drive member 1 such that the dose counter 48 is rotationally fixed to the drive member 1 and axially free to move. Moreover, the outer surface of the dose counter 48 carrying the markings 486 indicating the number of doses left in the cartridge 442 is increased compared to the embodiment shown in FIGS. 4A and 4B. This is enabled by the reduction of the number of parts of the drug delivery device 4 and the modified mechanism for driving the dose counter 48. The respective marking can be seen through a window (not visible here) in the dose button 465.

Moreover, the device 4 comprises an opening (not visible here) through which a marking indicating possible movements of the dose button 465 at certain phases of operation is visible. As an example, when a priming operation is required, the visible marking may be an arrow pointing to the distal direction 403 of the device 4.

The invention claimed is:

1. A drug delivery device comprising a drive member and an actuating member for driving the drive member, where the drive member comprises a longitudinal axis having a distal direction and a proximal direction,
   wherein the drive member is configured to be driven in a rotational movement around the longitudinal axis by an actuating member,
   wherein the drive member comprises a track having a contact face for transmitting a driving load from the actuating member to the drive member,
   wherein the track comprises sections running in the distal direction and sections running in the proximal direction of the drive member,
   wherein the drive member comprises a bias track having a contact face for transmitting a load from a component of a biasing means to the drive member for biasing the drive member towards a rotation around the longitudinal axis,
   wherein the device being configured to dispense a dose of a drug in a dose dispense operation as well as being configured to be prepared for a subsequent dose dispense operation in a dose set operation,
   wherein the biasing means is configured to bias the drive member at one end of the dose set operation and the dose dispense operation towards the rotation around the longitudinal axis, and
   wherein at the one end of the dose set operation the bias exerted by the biasing means results in a rotation of the drive member towards a position relative to the actuating member such that the subsequent dose dispense operation is enabled.

2. The drug delivery device of claim 1,
   wherein the track comprises at least one dose set section and at least one dose dispense section, wherein in an assembled form of the drug delivery device, the actuating member contacts the contact face on the dose set section for setting a dose and on the dose dispense section for dispensing the dose.

3. The drug delivery device of claim 1, wherein the bias track comprises a first redirecting section being inclined to the longitudinal axis.

4. The drug delivery device of claim 3, wherein the bias track comprises a second redirecting section being inclined to the longitudinal axis opposite to the first redirecting section.

5. The drug delivery device of claim 4, wherein the first and the second redirecting sections are adjacent to each other, thereby forming a recess in the bias track.

6. The drug delivery device of claim 1, comprising a coupling means configured to couple a piston rod to the drive member such that a relative translational movement of the drive member and the piston rod is allowed and a relative rotational movement is prevented.

7. The drug delivery device of claim 1, comprising a piston rod configured to be driven by the drive member in the dose dispense operation, wherein a relative rotational movement between the piston rod and the drive member is prevented and a relative axial movement is enabled.

8. The drug delivery device of claim 7,
wherein at an end of a dose dispense operation a torque exerted by the biasing means results in a rotation of the drive member such that the piston rod is moved in the proximal direction, thereby enabling a relaxation of a bung in a cartridge towards the proximal direction of the drug delivery device.

9. The drug delivery device of claim 1 comprising a threaded component being fixed to a housing of the drug delivery device, wherein the threaded component is threadedly engaged with the piston rod.

10. The drug delivery device of claim 1 comprising a dose member operable by a user, wherein the dose member serves as the actuating member for driving the drive member.

11. The drug delivery device of claim 10, wherein the dose member is configured for being pulled for setting the dose and to be pushed for dispensing the set dose.

\* \* \* \* \*